United States Patent
Huang et al.

(10) Patent No.: US 12,287,353 B2
(45) Date of Patent: Apr. 29, 2025

(54) METHOD FOR CHARACTERIZING INTERACTION FORCE BETWEEN LIGNIN AND CELLULASE

(71) Applicant: NANJING FORESTRY UNIVERSITY, Nanjing (CN)

(72) Inventors: Caoxing Huang, Nanjing (CN); Xiaoxue Zhao, Nanjing (CN); Qiang Yong, Nanjing (CN); Chenhuan Lai, Nanjing (CN); Yongcan Jin, Nanjing (CN)

(73) Assignee: NANJING FORESTRY UNIVERSITY, Nanjing (CN)

( * ) Notice: Subject to any disclaimer, the term of this patent is extended or adjusted under 35 U.S.C. 154(b) by 0 days.

(21) Appl. No.: 18/844,070

(22) PCT Filed: Aug. 31, 2023

(86) PCT No.: PCT/CN2023/116285
§ 371 (c)(1),
(2) Date: Sep. 5, 2024

(87) PCT Pub. No.: WO2024/060960
PCT Pub. Date: Mar. 28, 2024

(65) Prior Publication Data
US 2025/0110152 A1    Apr. 3, 2025

(30) Foreign Application Priority Data
Sep. 20, 2022    (CN) .......................... 202211147015.1

(51) Int. Cl.
*G01Q 60/38* (2010.01)
*C12Q 1/40* (2006.01)
*G01Q 60/28* (2010.01)
*G01Q 60/42* (2010.01)

(52) U.S. Cl.
CPC ............... *G01Q 60/42* (2013.01); *C12Q 1/40* (2013.01); *G01Q 60/28* (2013.01)

(58) Field of Classification Search
None
See application file for complete search history.

(56) References Cited

U.S. PATENT DOCUMENTS

| 2011/0275092 A1 | 11/2011 | Hu et al. | |
| 2013/0276176 A1* | 10/2013 | Polesel-Maris | G01Q 20/04 |
| | | | 850/40 |

FOREIGN PATENT DOCUMENTS

| CN | 104991090 A | | 10/2015 | |
| CN | 105754121 A | | 7/2016 | |
| CN | 107621555 A | | 1/2018 | |
| CN | 111505343 A | * | 8/2020 | ............. G01Q 60/24 |
| CN | 115541934 A | | 12/2022 | |

OTHER PUBLICATIONS

Jiang Chong, Investigating the effect of lignin on enzymatic hydrolysis of lignocellulosic biomass by quartz crystal microbalance, Nanjing Forestry University, 2017, pp. 1-45.

* cited by examiner

*Primary Examiner* — Nghi V Nguyen
(74) *Attorney, Agent, or Firm* — Bayramoglu Law Offices LLC

(57) ABSTRACT

A method for characterizing the interaction force between lignin and cellulase is provided. The method includes the following steps: (1) preparing a lignin solution, then dropwise adding the solution onto a silicon wafer, repeatedly spin-coating with a spin coater, and vacuum-drying the prepared lignin film; (2) modifying an AFM probe coated with a gold film on the surface with HS-PEG-COOH and then activating the carboxyl group, immersing the AFM probe after the carboxyl group activation in a PBS solution of cellulase for incubation, and after the modification is completed, placing the washed AFM probe in a PBS buffer solution for storage for later use; (3) testing the lignin-cellulase interaction force by using an AFM instrument in a liquid phase environment.

3 Claims, 28 Drawing Sheets

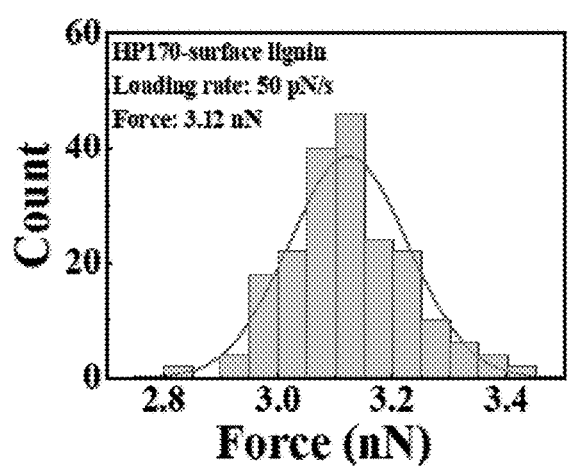
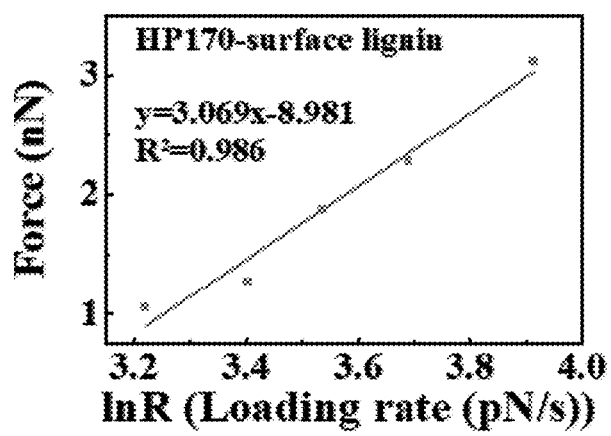
FIG. 2E
FIG. 2F

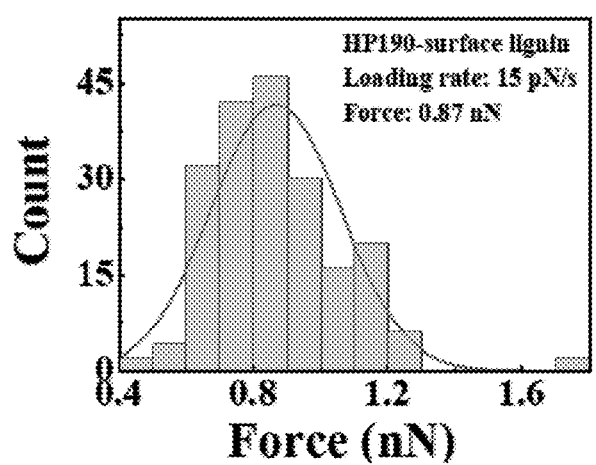 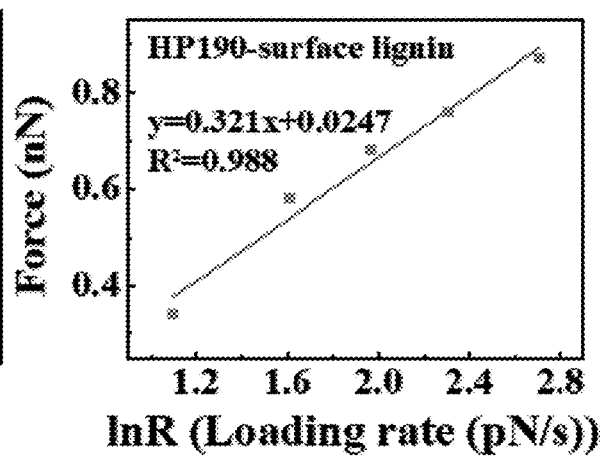
FIG. 3E
FIG. 3F

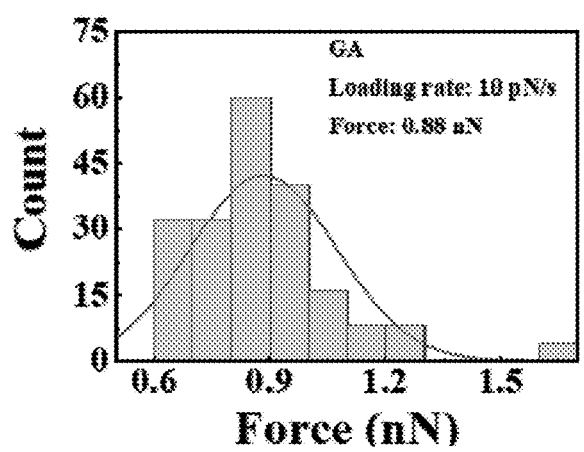
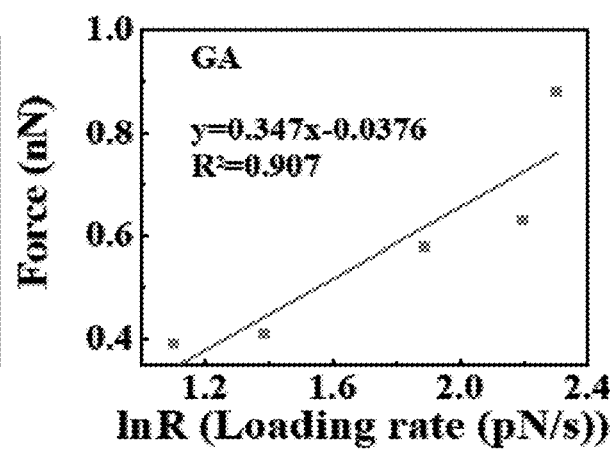
FIG. 11E
FIG. 11F

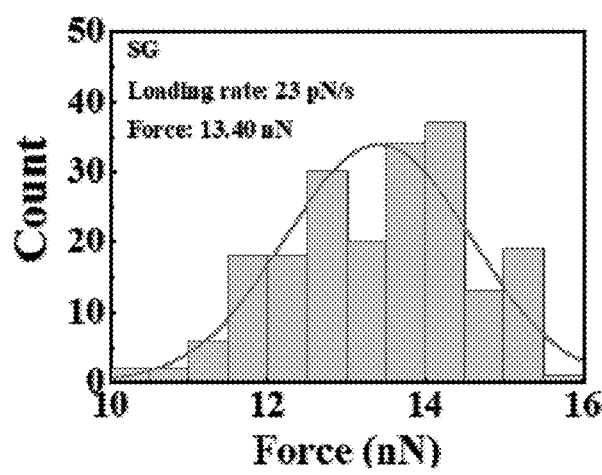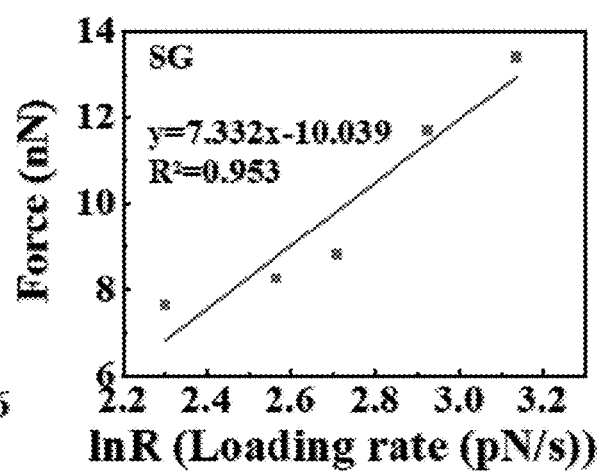
FIG. 12E
FIG. 12F

METHOD FOR CHARACTERIZING INTERACTION FORCE BETWEEN LIGNIN AND CELLULASE

CROSS REFERENCE TO THE RELATED APPLICATIONS

This application is the national phase entry of International Application No. PCT/CN2023/116285, filed on Aug. 31, 2023, which is based upon and claims priority to Chinese Patent Application No. 202211147015.1, filed on Sep. 20, 2022, the entire contents of which are incorporated herein by reference.

TECHNICAL FIELD

The invention belongs to the field of microscience, and more specifically, relates to a method for characterizing the interaction force between lignin and cellulase.

BACKGROUND

The production of bioethanol and liquid fuels by bioconversion of renewable lignocellulose is one of the effective ways to solve the shortage of fossil resources and ensure energy security. Among the many biorefining pathways, the hydrolysis of lignocellulose into fermentable monosaccharides by cellulase is a key step in the bioconversion of wood fiber. Specifically, direct contact between cellulase and cellulose is a necessary prerequisite for enzymatic hydrolysis. However, the non-productive binding of lignin and cellulase is considered to be one of the stubborn factors that hinder the accessibility of cellulose, which reduces the saccharification rate and the yield of carbohydrates, thereby increasing the saccharification cost of carbohydrates. Although the inhibitory effect of lignin on enzymatic hydrolysis is very important, its exact inhibitory mechanism is still controversial and needs to be further clarified.

At present, studying the interaction mechanism between surface lignin and residual lignin and cellulase during pretreatment is an important focus of wood fiber biorefining. It is generally believed that the physical and chemical properties of lignin, such as hydrophobicity, charge property, and functional groups, make lignin molecules and cellulase molecules adsorb to each other with a certain force, and the adsorbed cellulase is 'firmly' bound to lignin, reducing the free cellulase in the hydrolysis system, thereby reducing the cellulose saccharification efficiency. Due to the complexity of the interaction between wood fiber raw materials and cellulase, the glucose yield in the enzymatic hydrolysis process is still an important indicator to measure the efficiency of enzymatic hydrolysis of wood fiber raw materials. However, this measurement method has great limitations. It can only study the efficiency of cellulase hydrolysis of substrates, and cannot obtain the entire adsorption and desorption dynamic process and binding force from a microscale perspective, so as to analyze the interaction mechanism between lignin and cellulase.

With the rapid development of advanced analytical techniques, the interaction mechanism of lignin/surfactant-cellulase has made significant progress. Atomic force microscopy (AFM) can image proteins at the nanoscale with its high spatial resolution and force sensitivity and study the interaction between biomolecules within the range of piconewtons. It is currently widely used to quantitatively measure the interaction force between proteins and biomacromolecules. When lignin interacts with cellulase, the force required to separate them is usually called the 'adhesion force'.

SUMMARY

In view of the above problems existing in the prior art, the technical problem to be solved by the present invention is to provide a method for characterizing the interaction force between lignin and cellulase.

In order to solve the above technical problems, the technical scheme adopted by the present invention is as follows:

A method for characterizing the interaction force between lignin and cellulase, comprising the following steps:

(1) preparation of lignin film: preparing a lignin solution or a lignin model substance solution, then dropwise adding the solution onto a silicon wafer, repeatedly spin-coating with a spin coater, and vacuum-drying the prepared lignin film;

(2) AFM probe modification: modifying an AFM probe coated with a gold film on the surface with HS-PEG-COOH and then activating the carboxyl group, immersing the AFM probe after the carboxyl group activation in a phosphate buffer saline (PBS) solution of cellulase for incubation, and after the modification is completed, the washed AFM probe is placed in PBS buffer solution for storage for later use;

(3) testing the lignin-cellulase interaction force by using an AFM instrument in a liquid phase environment.

Furthermore, the specific method for preparing the lignin film is as follows:

0.5% (w/v, dimethylsulfoxide (DMSO)) lignin solution or lignin model substance solution is prepared, then 100 μL of the solution is dropwise added onto the silicon wafer with a flat mouth syringe, after the solution diffuses to the entire surface of the silicon wafer, it is left for 1 min, and a spin coater is used to spin coat at a speed of 5000 r/min for 1 min, repeat 3 times; the prepared lignin film is vacuum dried at 40° C. for 4 h, and then soaked in deionized water for 1 day; the deionized water is replaced every 2 h to ensure that DMSO is completely removed to avoid affecting the activity of cellulase; the soaked film is vacuum dried at 40° C. for 12 h.

Furthermore, the specific method of modifying the AFM probe is as follows:

The AFM probe coated with a gold film on the surface is immersed in a DMSO solution of 0.2 mg/mL HS-PEG-COOH and incubated at room temperature in the dark for 3 h; the polyethylene glycol (PEG)-modified probe is washed three times with DMSO, placed in warm water less than 50° C., and left to stand for 30 min to remove the PEG molecules physically adsorbed on the probe surface; then the AFM probe is immersed in a 10 mM N-Hydroxysuccinimide (NHS)/1-(3-Dimethylaminopropyl)-3-ethylcarbodimide (EDC) mixed PBS buffer and incubated at room temperature for 30 min; the carboxyl-activated AFM probe is immersed in a PBS solution of cellulase and incubated overnight at 4° C. in the dark; after the modification is completed, the AFM probe is washed three times with PBS solution and placed in PBS buffer solution for storage for later use.

Furthermore, the molar mass of the cellulase PBS solution is 0.2 μM, and the pH is 7.4.

Furthermore, the binding ability of lignin and cellulase is evaluated by the dissociation rate constant of the interaction reaction. After counting several representative force-displacement curves at each loading rate, the dissociation force of lignin and cellulase is calculated using the following Bell-Evans equation:

$$F = \frac{k_B T}{x_\beta} \times \ln \frac{R x_\beta}{k_B T k_{off}}$$

Where F represents the dissociation force, $X_\beta$ is the distance from the lowest energy point of the binding state to the molecular activation state on the dissociation path, R is the dissociation force loading rate, $R = k_{eff} \times v$, where $k_{eff}$ is the effective elastic coefficient of the AFM probe cantilever, and v is the retraction rate of the probe, $k_{off}$ is the dissociation rate constant when the lignin-cellulase interaction force is zero, T is the thermodynamic temperature, and $k_B$ is the Boltzmann constant.

Further, the lignin model substance is one or more of the following substances:

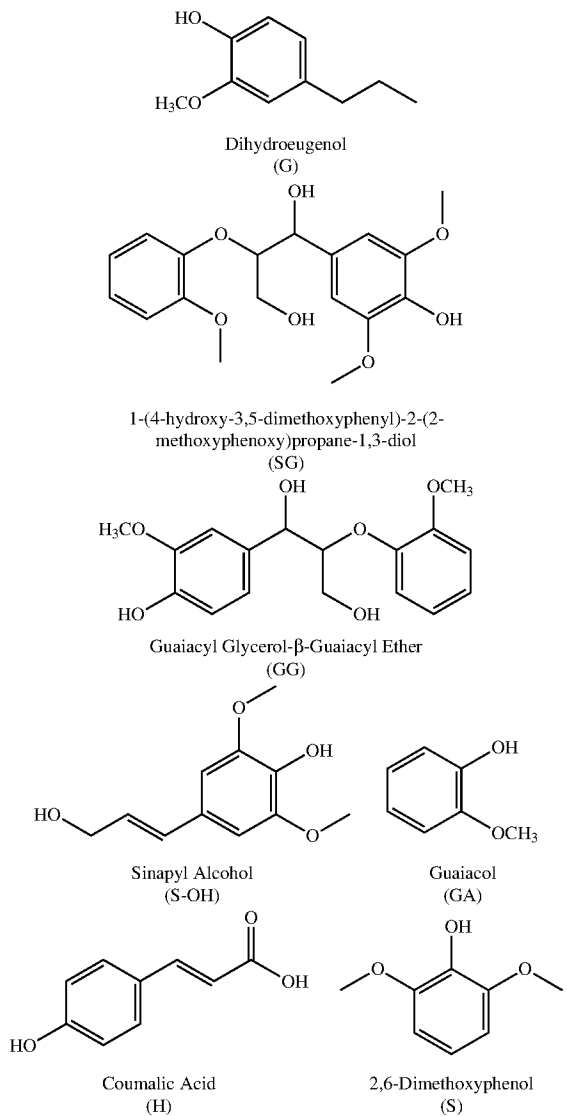

Dihydroeugenol (G)

1-(4-hydroxy-3,5-dimethoxyphenyl)-2-(2-methoxyphenoxy)propane-1,3-diol (SG)

Guaiacyl Glycerol-β-Guaiacyl Ether (GG)

Sinapyl Alcohol (S-OH)

Guaiacol (GA)

Coumalic Acid (H)

2,6-Dimethoxyphenol (S)

Compared with the prior art, the beneficial effects of the present invention are as follows:

AFM probes can be modified to have specific chemical or even biochemical properties, so that AFM can characterize the interaction force between specific protein molecules and ligands at the nanometer level. It can also be used to characterize surface morphology in various fields from the submolecular level to the cellular level. Through the results, we can observe the dynamic changes experienced by individual molecules in the physiological environment and manipulate polymers at the molecular level. Therefore, the present invention uses AFM to evaluate the interaction force and dissociation rate between enzymes (proteins) and lignin (biomacromolecules) to quantitatively characterize the interaction between the two in a liquid environment. At present, this method is the only one that can characterize the nanoscale interaction between lignin and cellulase in a liquid phase environment. The relevant characterization results show that:

1) Compared with the lignin on the surface of the pretreated material, the residual lignin has a stronger interaction force with the cellulase, resulting in a decrease in the content of free cellulase during the enzymatic hydrolysis process, thereby resulting in a lower substrate enzymatic hydrolysis yield.
2) As the pretreatment temperature increases, the interaction force between the lignin/residual lignin on the surface of the material and the cellulase decreases, and the dissociation rate increases.
3) The interaction force between the three common lignin monomers and cellulase is H>S>G, which is consistent with its inhibitory effect on enzymatic hydrolysis.
4) The interaction force between the dimer and cellulase is stronger than that between the monomer model and cellulase. In addition, steric hindrance, methoxyl group, and aliphatic hydroxyl group are still important factors leading to the non-productive binding of lignin and cellulase.
5) Compared with lignin in the material, the dissociation rate of lignin model substance and cellulase is smaller, indicating that lignin model substance is less likely to dissociate after binding with cellulase.

It can be seen that AFM has a wider application in characterizing the interaction force between lignin and cellulase.

BRIEF DESCRIPTION OF THE DRAWINGS

(FIG. 1A: surface lignin; FIG. 1B: residual lignin);

FIGS. 2A-2F show the force statistical histogram and dissociation rate fitting diagram of surface lignin and cellulase at different loading force speeds under 170° C. hydrothermal pretreatment conditions;

FIGS. 3A-3F show the force statistical histogram and dissociation rate fitting diagram of surface lignin and cellulase at different loading force speeds under 190° C. hydrothermal pretreatment conditions;

FIGS. 11A-11F are the force statistical histogram and dissociation rate fitting diagram of GA and cellulase at different loading force speeds;

FIGS. 12A-12F are the force statistical histogram and dissociation rate fitting diagram of SG and cellulase at different loading force speeds;

DETAILED DESCRIPTION OF THE EMBODIMENTS

Figure 1A:
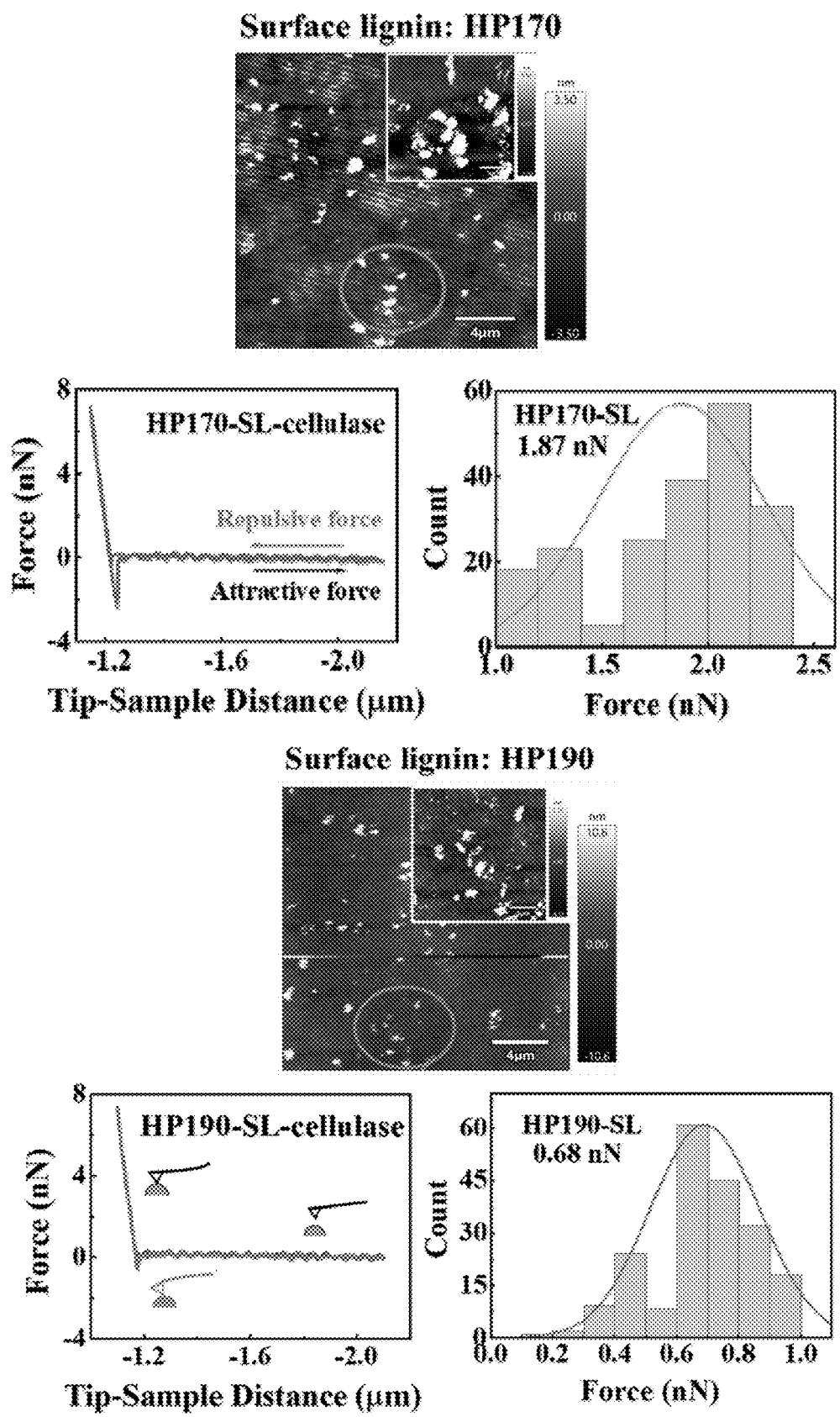
FIGS. 1A-1B show the morphologies of surface lignin and residual lignin of poplar wood under hydrothermal pretreatment at different temperatures; the force-displacement curves and force distribution histograms of surface lignin, residual lignin and cellulase of poplar wood under hydrothermal pretreatment at different temperatures.

In order to make the purpose, technical scheme, and advantages of the present invention clearer, the present invention is further described in conjunction with specific examples.

Example 1: Analysis of the Interaction Force Between Lignin and Cellulase in a Liquid Phase Environment 1. Preparation of Pretreated Materials A small oil bath digester (reactor volume of 150 mL) was used for hydrothermal pretreatment of poplar sawdust. 10 g of absolutely dry poplar sawdust was placed in a reactor, and distilled water was added at a solid-liquid ratio of 1:10, and the reaction was carried out at 170° C. and 190° C. for 1 hour respectively. After the reaction was completed, the reactor was quickly taken out, and after cooling, the reaction materials were separated into solid and liquid using a desktop circulating vacuum pump and a suction filtration device. The separated pretreatment residue was washed with distilled water until neutral, and placed in a 4° C. refrigerator for later use. The pretreated poplar wood was named based on the pretreatment temperature: the 170° C. hydrothermal pretreatment poplar wood was named HP-170, and the 190° C. hydrothermal pretreatment poplar wood was named HP-190.

2. Preparation of Surface Lignin 20 g of HP-170 and HP-190 pretreatment residues were respectively weighed into conical flasks, 200 mL of 1,4-dioxane/water (96:4, v/v) solution was added at a solid-liquid ratio of 1:10, conical flasks were placed on a magnetic stirrer at 150 r/min at room temperature and extracted for 1 day. After the end, solid-liquid separation was conducted by centrifugation, and fresh organic extraction solution was added to the extracted solids to continue extraction. The above process was repeated three times to ensure that the surface lignin was extracted to the maximum extent. The supernatant was collected three times and mixed together, the extraction solvent was removed by rotary evaporation and vacuum freeze drying to obtain surface lignin solids, which were labelled as 170-surface lignin (170-SL) and 190-surface lignin (190-SL) according to the pretreatment temperature.

The remaining solid material after extraction was then washed with a large amount of distilled water and air-dried to ensure the complete removal of the organic solvent, and collected in a ziplock bag for later use.

3. Preparation of Residual Lignin 5 g of each absolutely dry residue obtained after the extraction of surface lignin in step 2 was weighed and put into a planetary ball mill (Pulverisette7, Fritsch, Germany), 25 zirconia balls with a diameter of 1 cm were used to grind at a speed of 600 r/min for 6 h. The residual lignin in the poplar sawdust was obtained by the Björkman method. They were labelled as 170-residual lignin (170-RL) and 190-residual lignin (190-RL) according to different pretreatment temperatures.

4. Analysis of the Interaction Force Between Lignin and Cellulase in Liquid Phase Environment (1) Preparation of lignin film: 0.5% (w/v, DMSO) lignin solution [surface lignin series (170-SL, 190-SL) and residual lignin series (170-RL, 190-RL)] was prepared, then 100 μL of the solution was dropwise added onto the silicon wafer with a flat mouth syringe, after the solution diffused to the entire surface of the silicon wafer, it was left for 1 min, and a spin coater (KW-4A, Shanghai Daojing Instrument Factory, China) was used to spin coat at a speed of 5000 r/min for 1 min, and repeat 3 times. The prepared lignin film was vacuum dried at 40° C. for 4 h, and then soaked in deionized water for 1 day. The deionized water was replaced every 2 h to ensure that DMSO was completely removed to avoid affecting the activity of cellulase. The soaked film was vacuum dried at 40° C. for 12 h.

(2) AFM probe modification: The AFM probe coated with a gold film on the surface was immersed in a 0.2 mg/mL HS-PEG-COOH DMSO solution and incubated at room temperature for 3 h in the dark. After washing the PEG-modified probe with DMSO three times, it was placed in warm water less than 50° C. and allowed to stand for 30 min to remove the PEG molecules physically adsorbed on the probe surface. Then the AFM probe was immersed in a 10 mM NHS/EDC mixed PBS buffer and incubated at room temperature for 30 min. The carboxyl-activated AFM probe was immersed in a PBS solution of cellulase (0.2 μM, pH=7.4) and incubated at 4° C. in the dark overnight. After the modification, the AFM probe was washed three times with PBS solution and placed in PBS buffer solution for storage for later use.

Figure 1B:
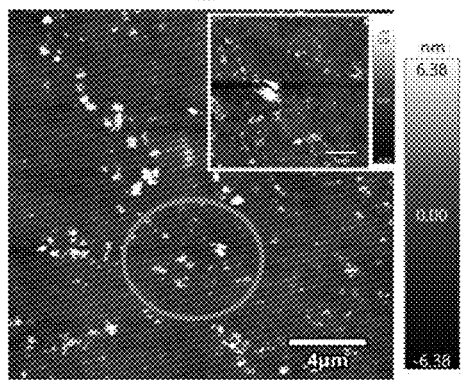
Figure 1B:
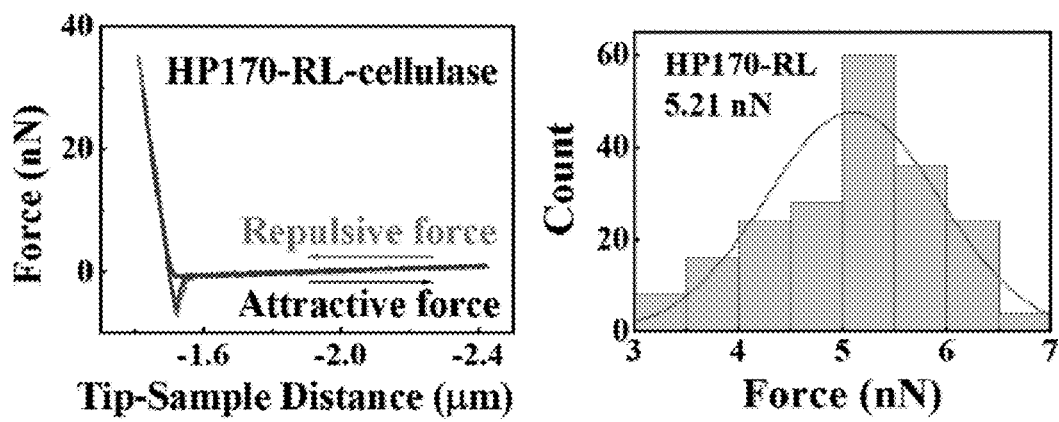
Figure 1B:
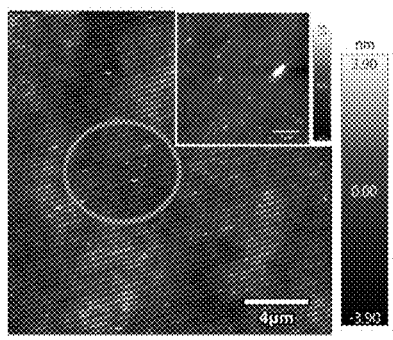
Figure 1B:
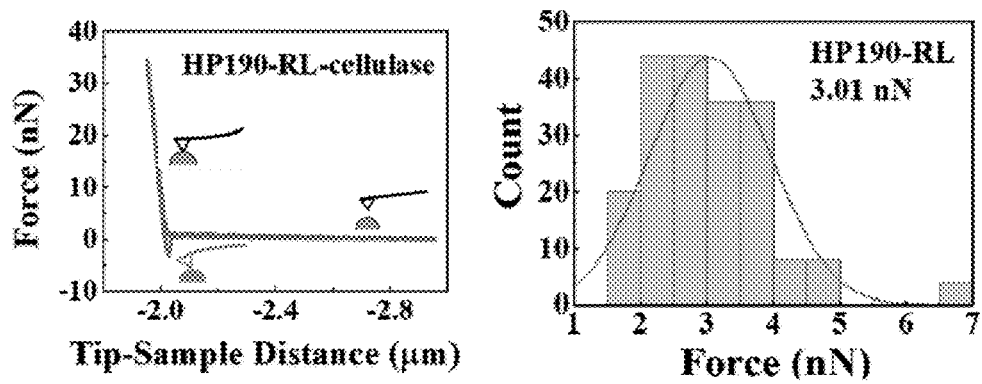
Figure 2A:
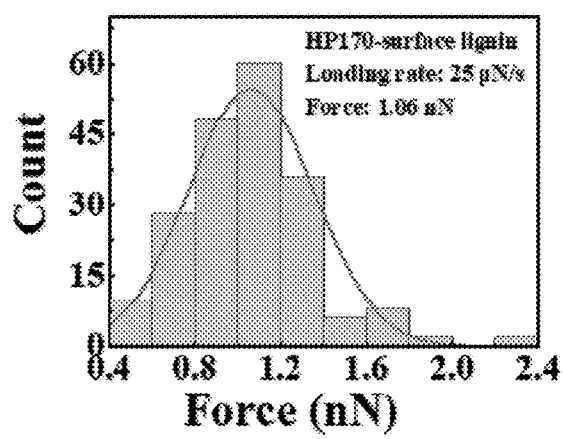
Figure 2B:
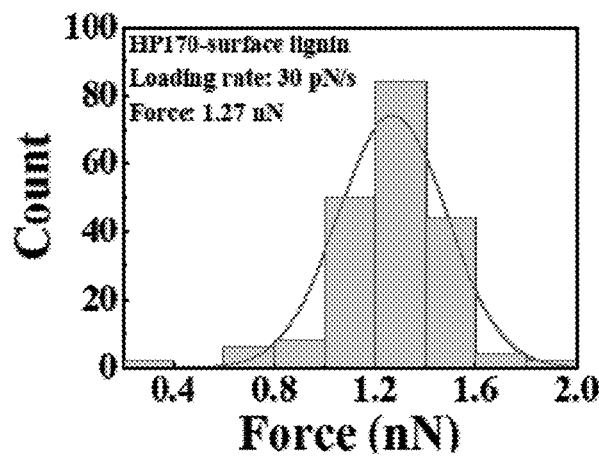
Figure 2C:
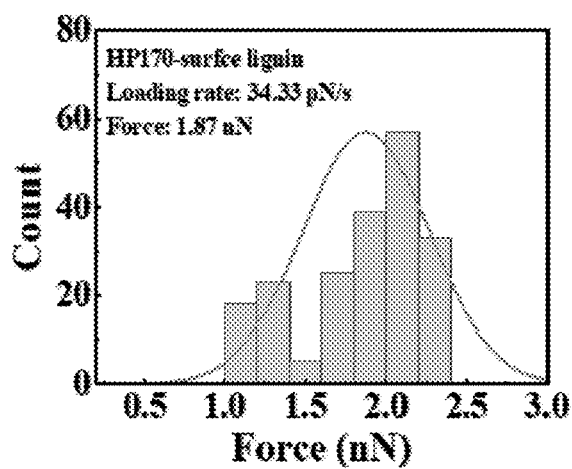
Figure 2D:
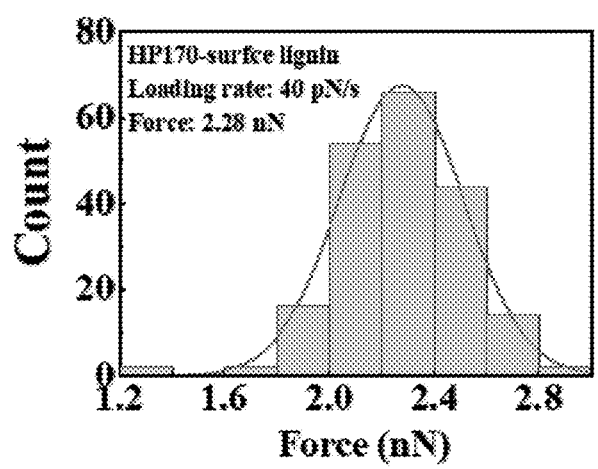
Figure 3A:
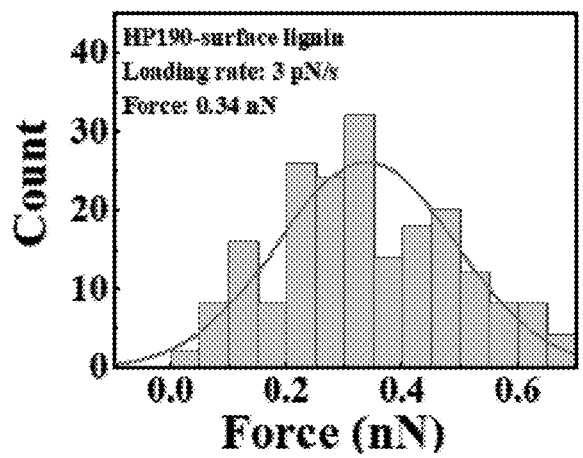
Figure 3B:
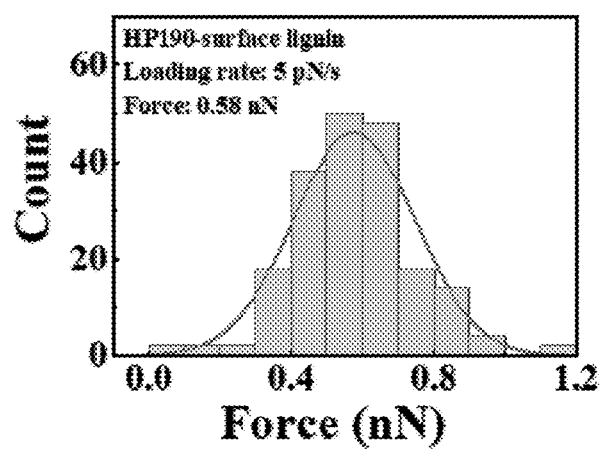
Figure 3C:
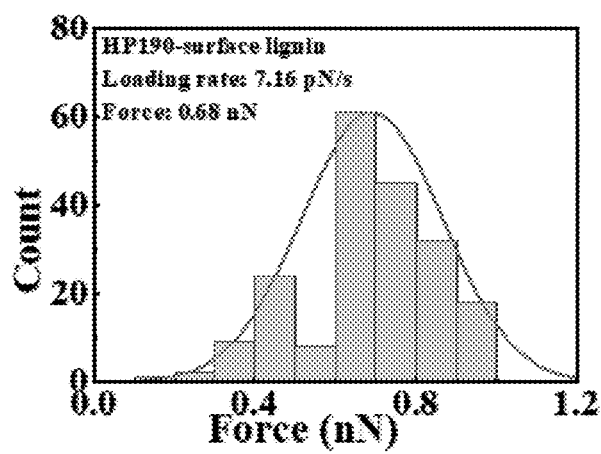
Figure 3D:
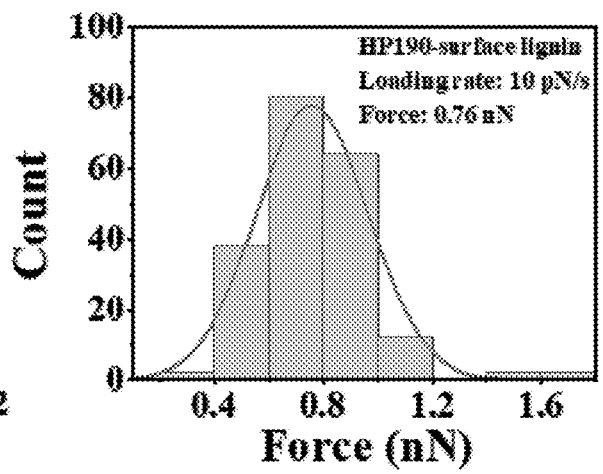
Figure 4A:
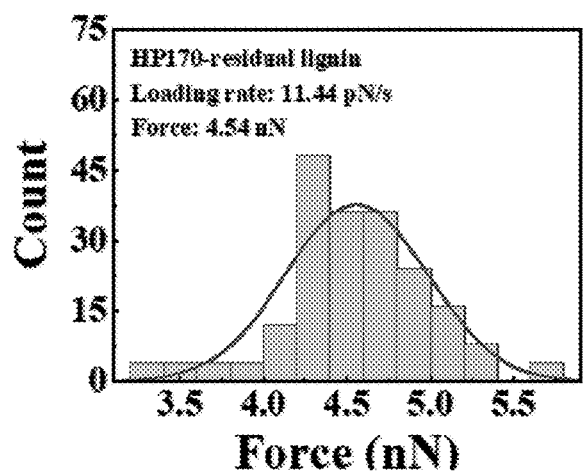
FIGS. 4A-4E show the force statistical histogram and dissociation rate fitting diagram of residual lignin and cellulase at different loading force speeds under 170° C. hydrothermal pretreatment conditions.
Figure 4B:
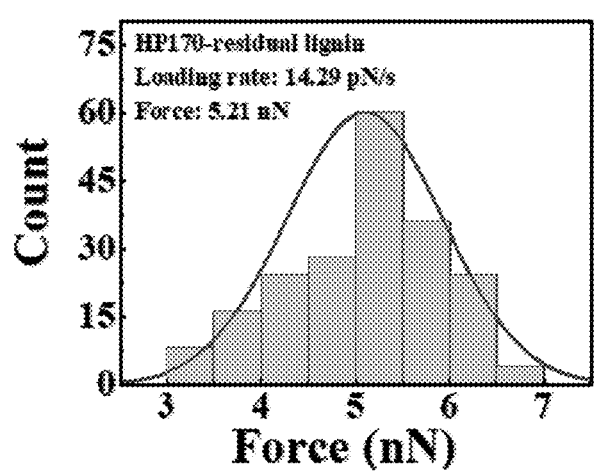
Figure 4C:
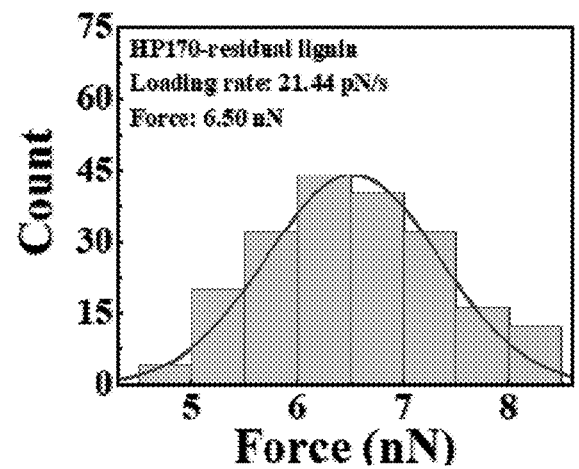
Figure 4D:
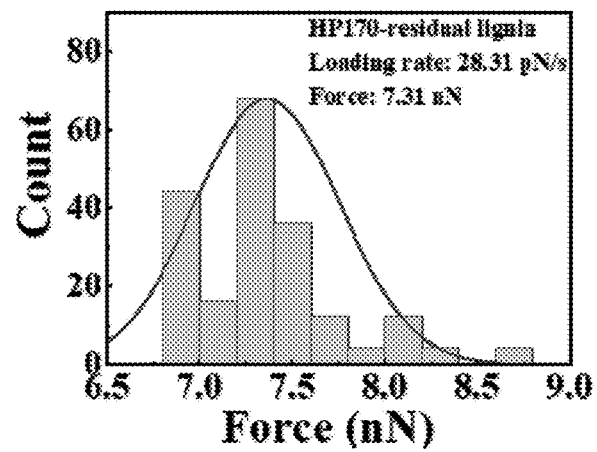
Figure 4E:
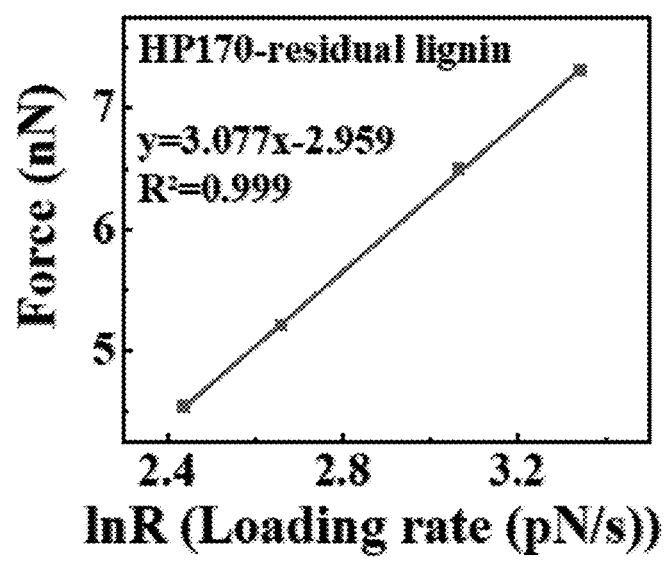
Figure 5A:
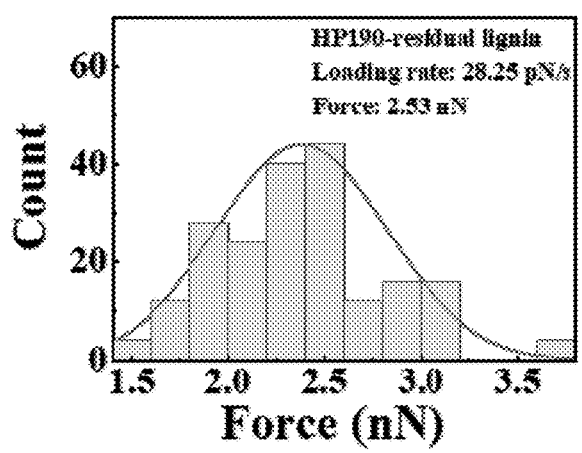
FIGS. 5A-5E show the force statistical histogram and dissociation rate fitting diagram of residual lignin and cellulase at different loading force speeds under 190° C. hydrothermal pretreatment conditions.
Figure 5B:
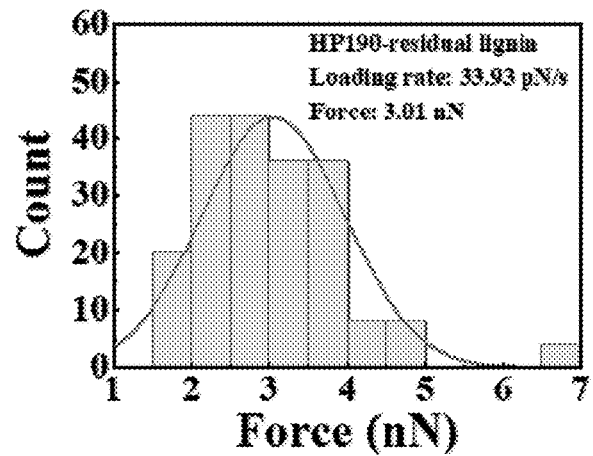
Figure 5C:
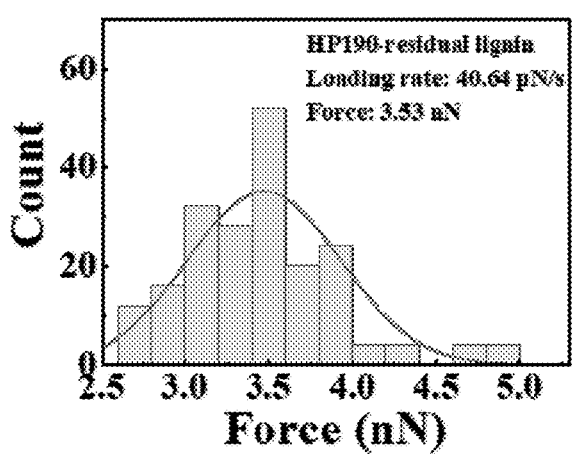
Figure 5D:
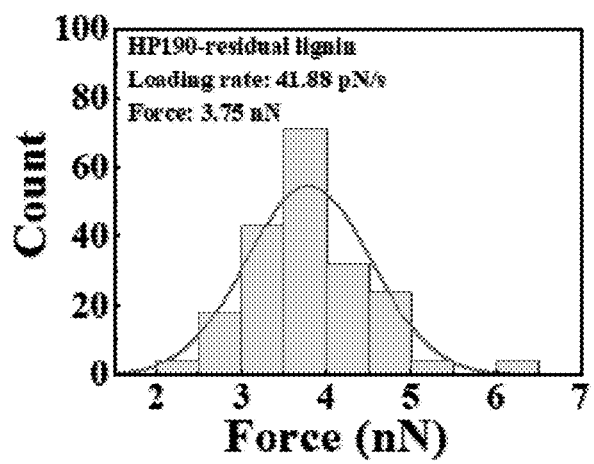
Figure 5E:
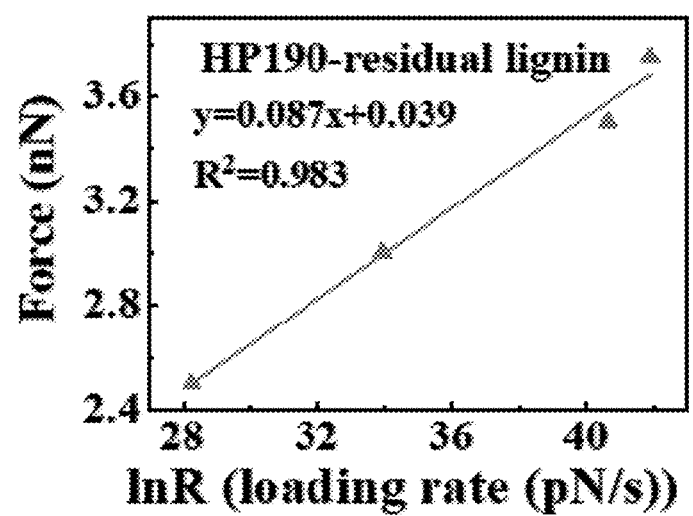

(3) Test of lignin-cellulase interaction force in liquid phase environment: The AC Air Topography and AC Water Topography modes of the AFM instrument (MFP-3D origin, Asylum research, Oxford Instruments, UK) were used to obtain the morphological recognition map of lignin fixed on the silicon wafer surface and the force-displacement curves and interaction forces between cellulase and different lignins (FIGS. 1A-1B). As can be seen from FIGS. 1A-1B, the interaction forces between surface lignin and cellulase under hydrothermal pretreatment conditions of 170° C.

and 190° C. were 1.87 nN and 0.68 nN, respectively. The interaction forces between residual lignin and cellulase in hydrothermally pretreated poplar wood were 5.21 nN and 3.01 nN, respectively. The results show that the interaction force between residual lignin and cellulase in hydrothermally pretreated poplar wood is stronger than that between surface lignin and cellulase, and the interaction force weakens with the increase of pretreatment intensity.

In addition, the binding ability of lignin and cellulase can also be evaluated by the dissociation rate constant of the interaction reaction. After counting 200 representative force-displacement curves at each loading rate, the dissociation force between lignin and cellulase was calculated using the following Bell-Evans equation:

$$F = \frac{k_B T}{x_\beta} \times \ln \frac{R x_\beta}{k_B T k_{off}} \quad (1)$$

Where F represents the dissociation force, $X_\beta$ is the distance from the lowest energy point of the binding state to the molecular activation state on the dissociation path, R is the dissociation force loading rate, $R=k_{eff} \times v$, where $k_{eff}$ is the effective elastic coefficient of the AFM probe cantilever, and v is the retraction rate of the probe, $k_{off}$ is the dissociation rate constant when the lignin-cellulase interaction force is zero, T is the thermodynamic temperature, and $k_B$ is the Boltzmann constant.

At the single-molecule level, AFM can be used to detect the dissociation rate of the interaction between the lignin molecules modified on the substrate and the cellulase protein modified on the tip of the AFM probe. The force histogram and dissociation rate fitting diagram of surface lignin and residual lignin of poplar wood and cellulase at different force loading rates under hydrothermal conditions are shown in FIGS. 2A-5E.

As shown in FIGS. 2A-2F, the most likely dissociation forces between HP-170-SL and cellulase at five different loading rates (25 pN/s, 30 pN/s, 34.33 pN/s, 40 pN/s, 50 pN/s) were 1.06 nN, 1.27 nN, 1.87 nN, 2.28 nN, and 3.12 nN, respectively. As shown in FIGS. 3A-3F, the most likely dissociation forces between HP-190-SL and cellulase at five different loading rates (3 pN/s, 5 pN/s, 7.16 pN/s, 10 pN/s, and 15 pN/s) were 0.34 nN, 0.58 nN, 0.68 nN, 0.76 nN, and 0.87 nN, respectively. As shown in FIGS. 4A-4E, the most likely dissociation forces between HP-170-RL and cellulase at four different loading rates (11.44 pN/s, 14.29 pN/s, 21.44 pN/s, 28.31 pN/s) were 4.54 nN, 5.21 nN, 6.50 nN, and 7.31 nN, respectively. As shown in FIGS. 5A-5E, the most likely dissociation forces between HP-190-SL and cellulase at four different loading rates (28.25 pN/s, 33.93 pN/s, 40.64 pN/s, and 41.88 pN/s) were 2.53 nN, 3.01 nN, 3.53 nN, and 3.75 nN, respectively. In order to calculate the dissociation rate constant ($k_{off}$) of the interaction between lignin modified on the substrate surface and cellulase, the Bell-Evans model of formula 1 was used to perform linear fitting with lnR as the horizontal coordinate and F as the vertical coordinate. The results are shown in Table 1. As shown in Table 1, the dissociation rates of HP-170-SL, HP-190-SL, HP-170-RL, and HP-190-RL were 6.08 s$^{-1}$, 3.36 s$^{-1}$, 0.84 s$^{-1}$, and 7.36 s$^{-1}$, respectively. The low dissociation rate constant indicates that the lignin modified on the substrate surface has a higher affinity with cellulase, that is, the less likely it is to dissociate after the two are combined. The above data shows that HP-170-RL has the strongest interaction with cellulase, and it is less likely to dissociate after combining. This may be related to the structure of lignin under this pretreatment condition, which makes it easier to interact with cellulase.

In summary, the above results prove that the AFM method can be used to evaluate the interaction force and dissociation rate between surface lignin/residual lignin of pretreated materials and cellulase in liquid environment, which is conducive to further analysis of the interaction mechanism between lignin and cellulase, laying a solid theoretical foundation for the next step of scientific research and has good practicality.

TABLE 1

Dissociation rate of surface lignin, residual lignin and cellulase

| System | $F_{eq}$ (nN) | $k_{off}$ (s$^{-1}$) |
| --- | --- | --- |
| HP170-SL-cellulase | 1.87 | 6.08 |
| HP190-SL-cellulase | 0.68 | 3.36 |
| HP170-RL-cellulase | 5.21 | 0.84 |
| HP190-RL-cellulase | 3.01 | 7.36 |

Figure 6:
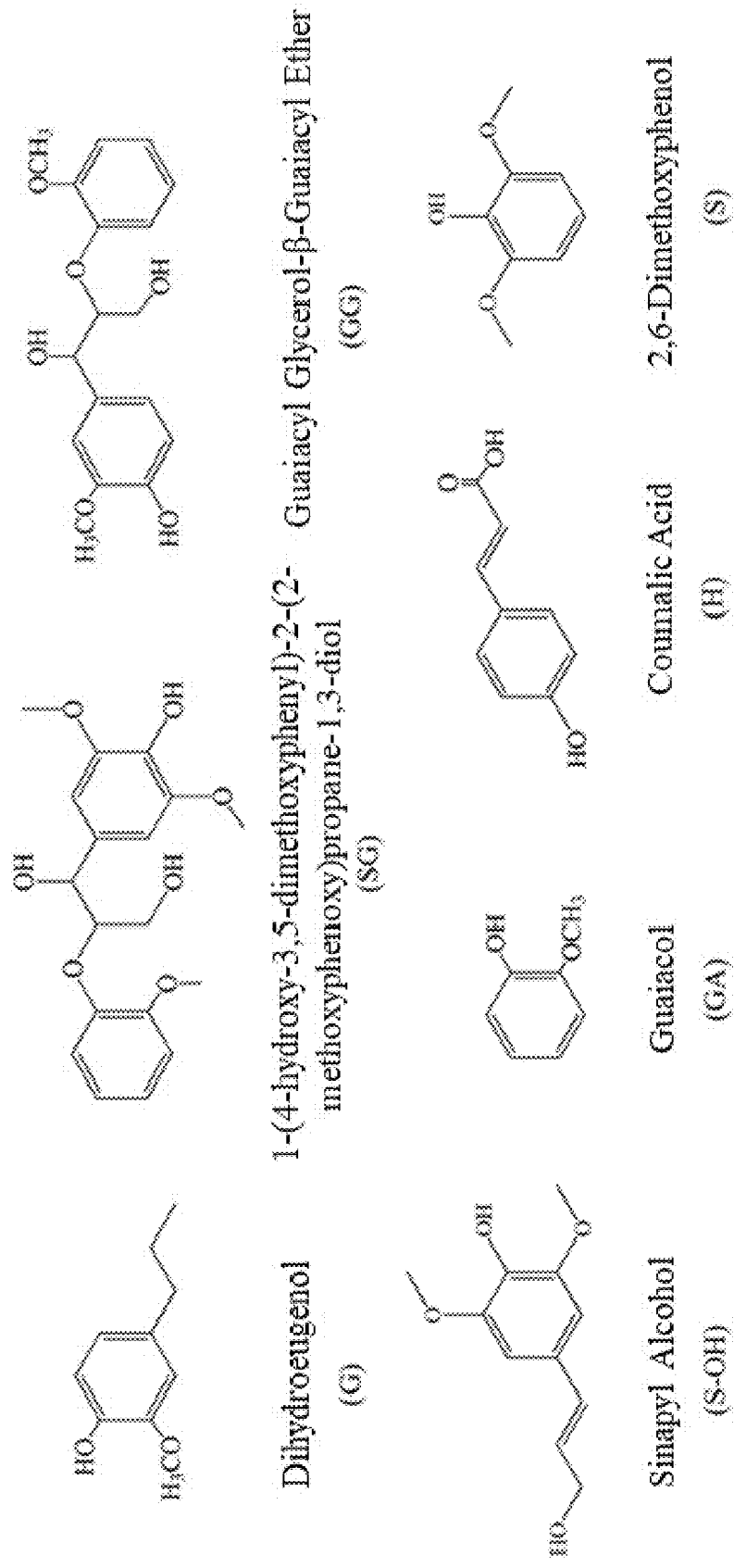
FIG. 6 shows the chemical structure of different lignin model substances.
Figure 7:
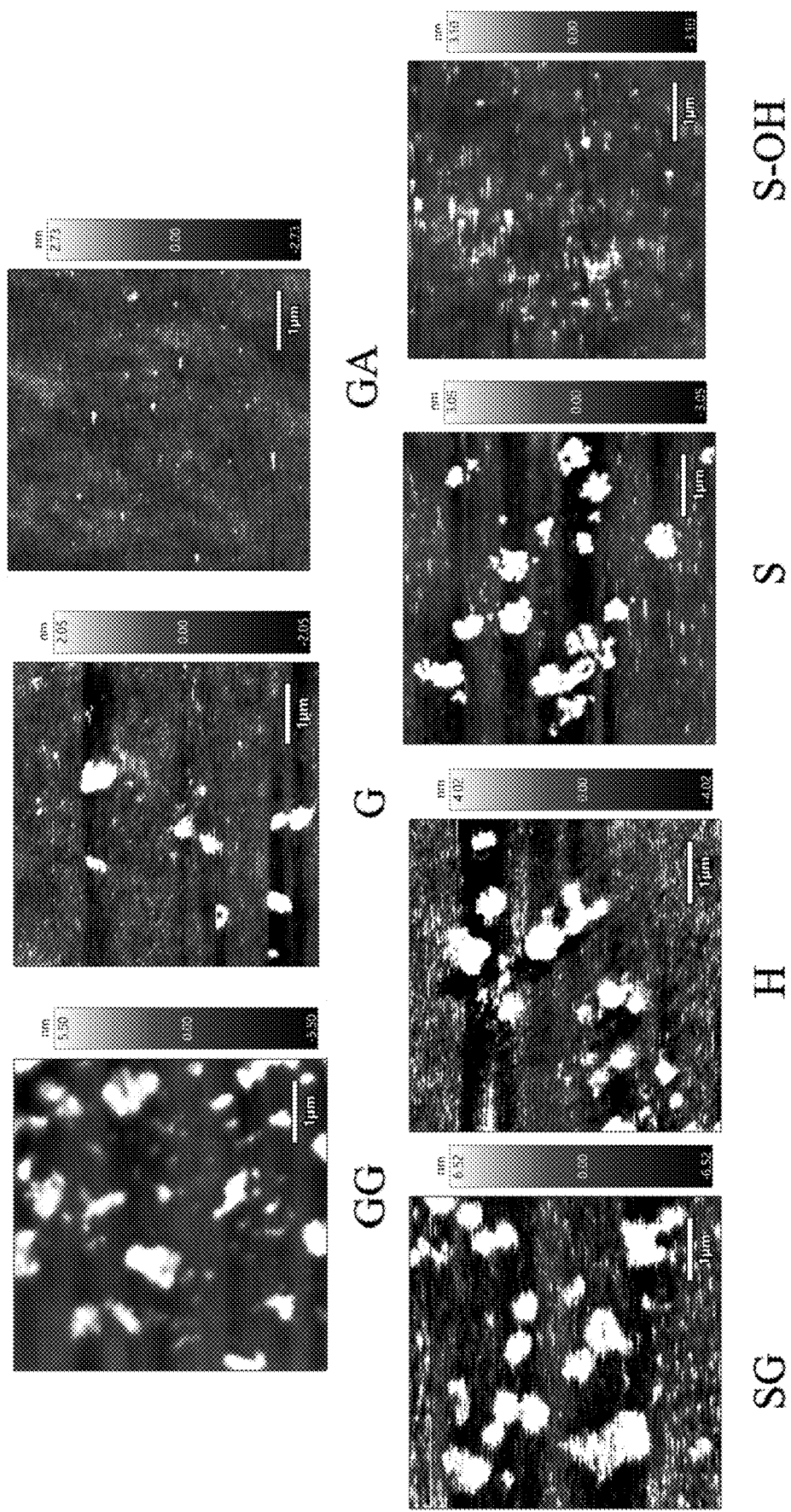
FIG. 7 is the morphologies of different lignin model substances.
Figure 8A:
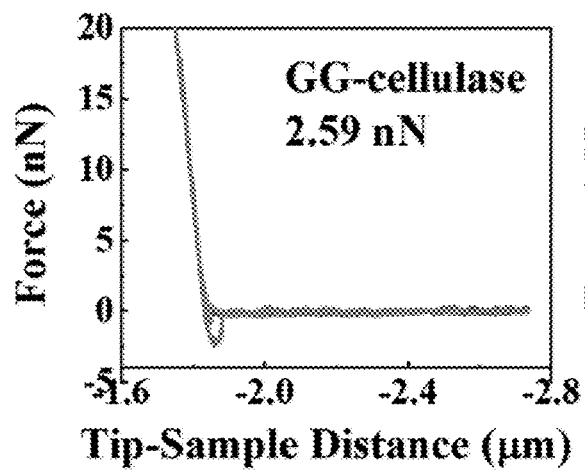
FIGS. 8A-8G are the force-displacement curve of different lignin model substances.
Figure 8B:
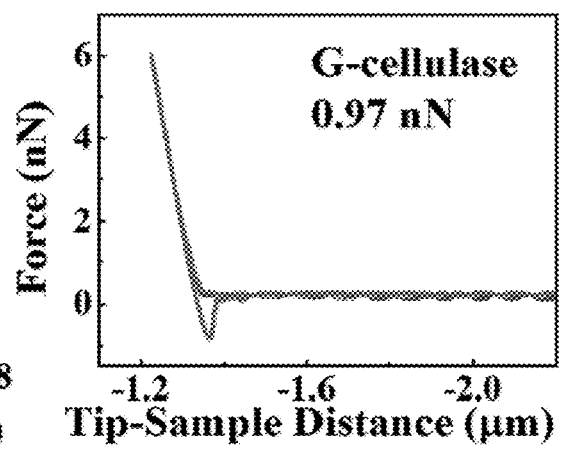
Figure 8C:
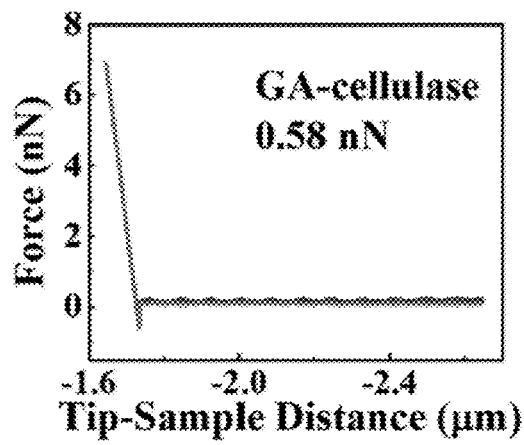
Figure 8D:
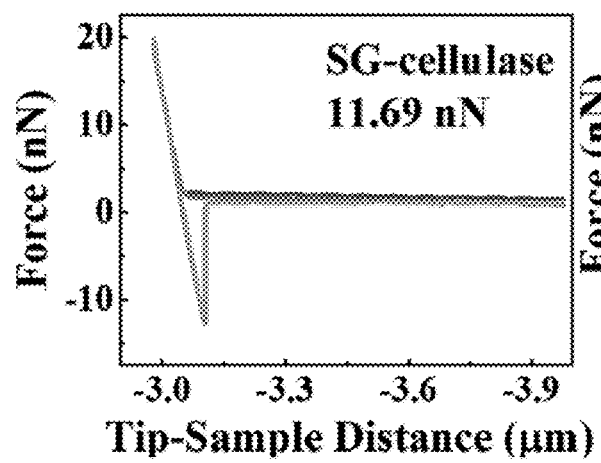
Figure 8E:
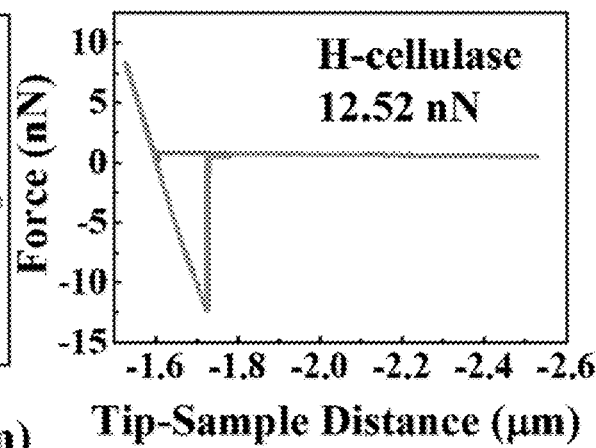
Figure 8F:
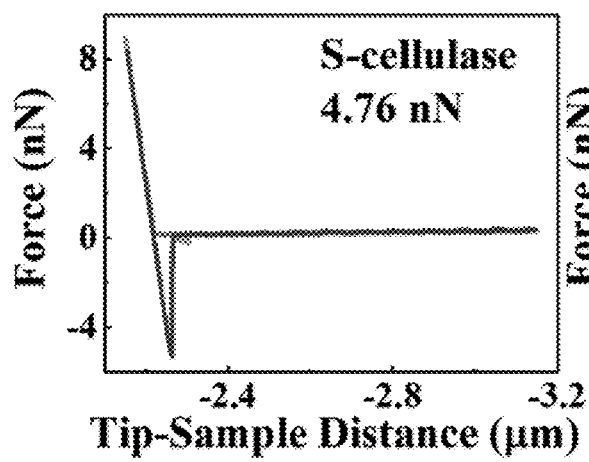
Figure 8G:
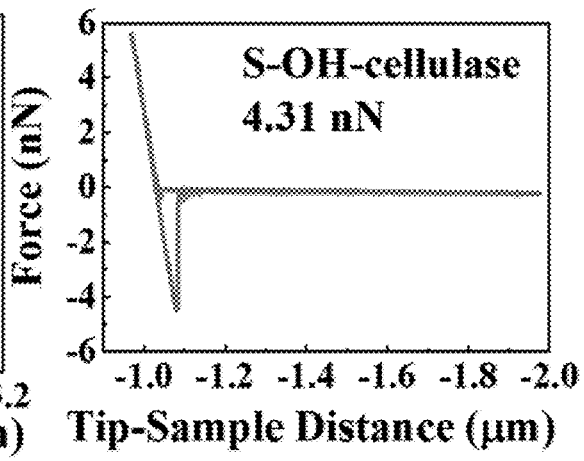
Figure 9A:
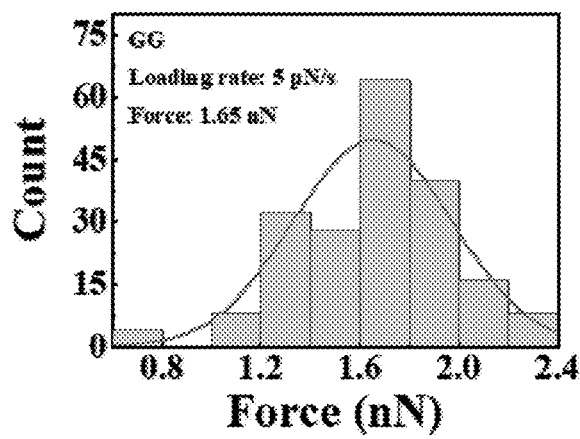
FIGS. 9A-9F are the force statistical histogram and dissociation rate fitting diagram of GG and cellulase at different loading force speeds.
Figure 9B:
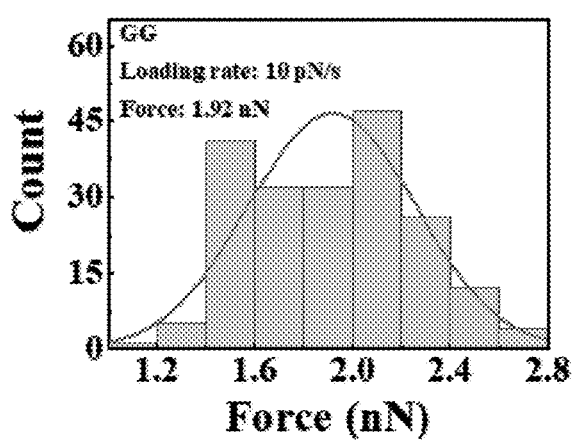
Figure 9C:
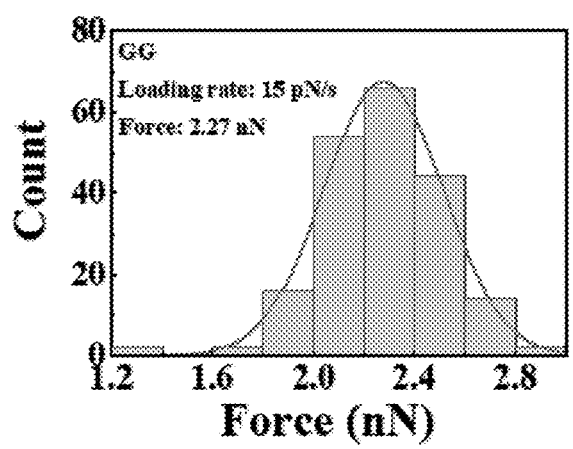
Figure 9D:
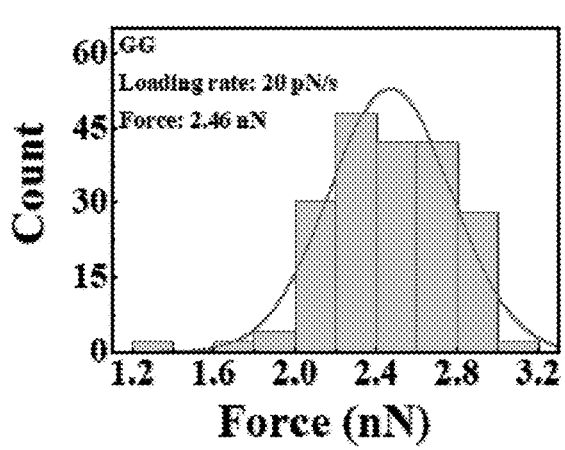
Figure 9E:
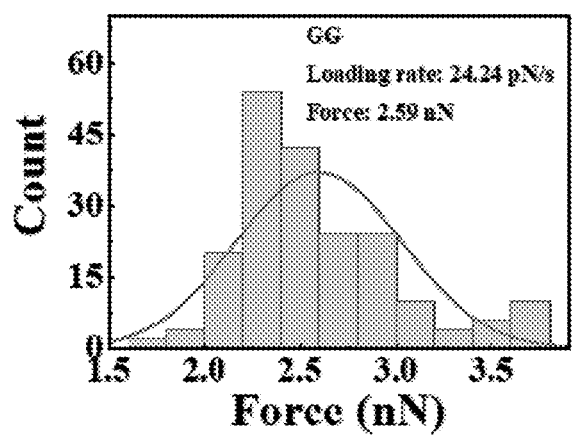
Figure 9F:
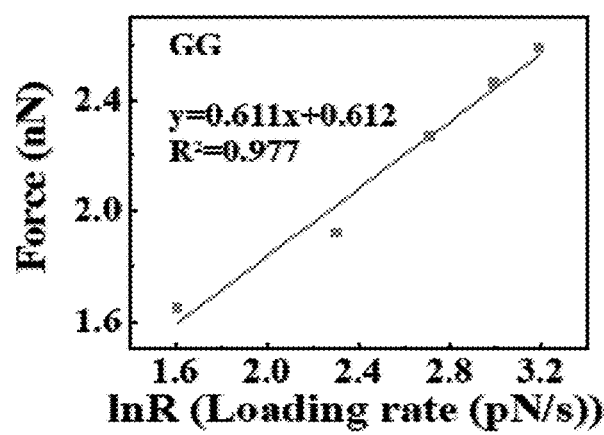
Figure 10A:
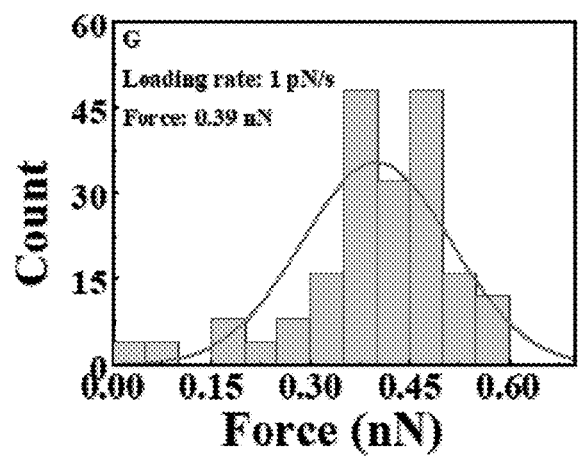
FIGS. 10A-10F are the force statistical histogram and dissociation rate fitting diagram of G and cellulase at different loading force speeds.
Figure 10B:
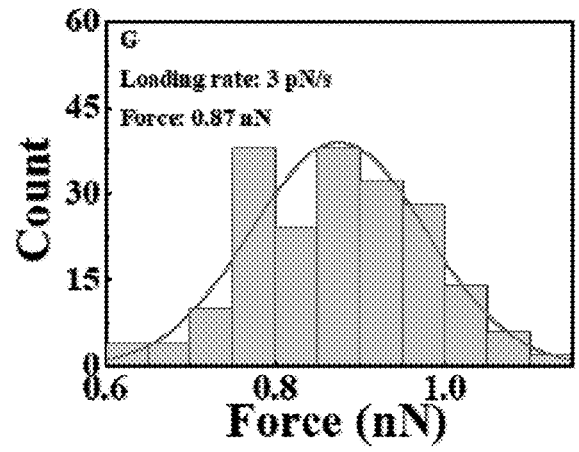
Figure 10C:
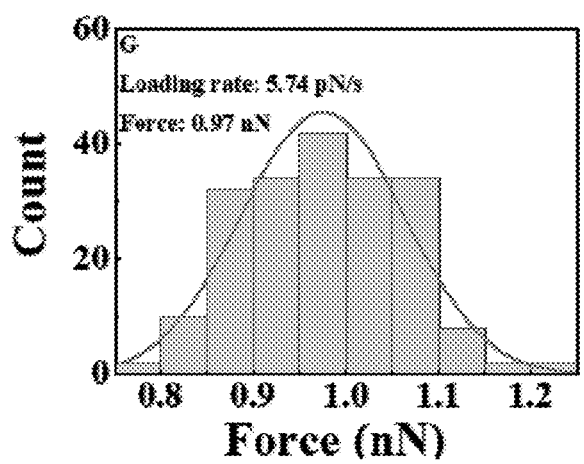
Figure 10D:
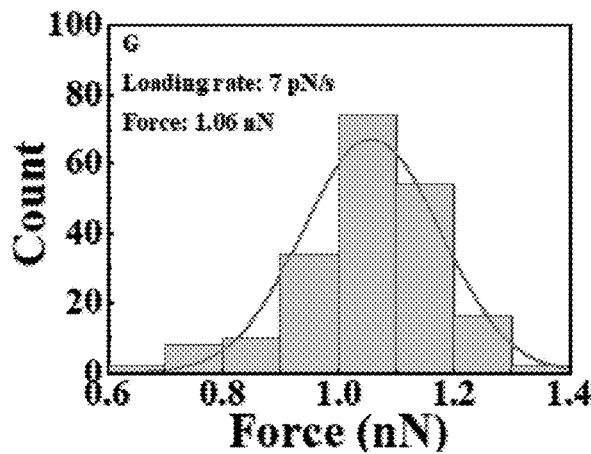
Figure 10E:
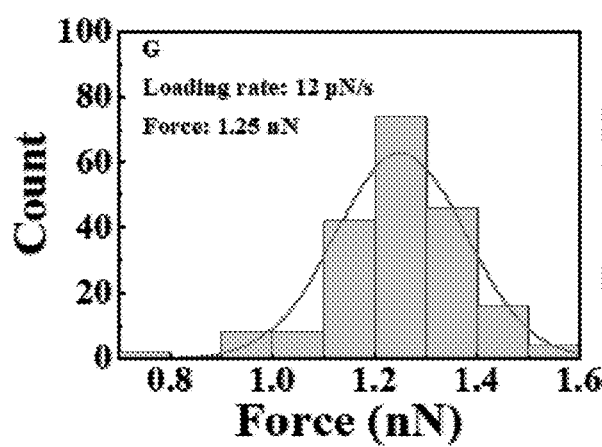
Figure 10F:
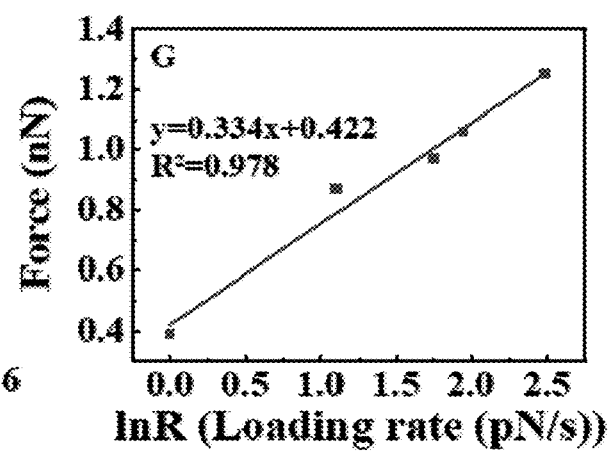
Figure 11A:
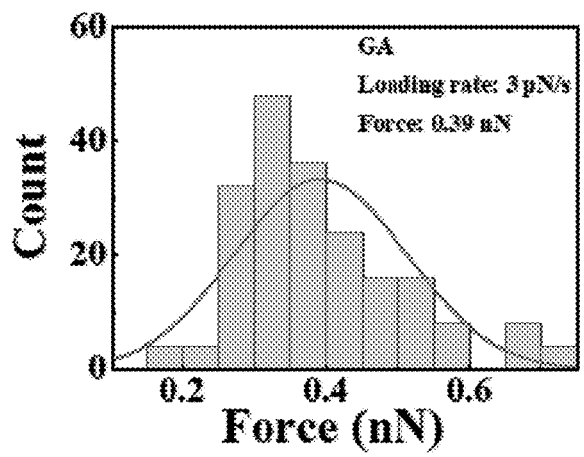
Figure 11B:
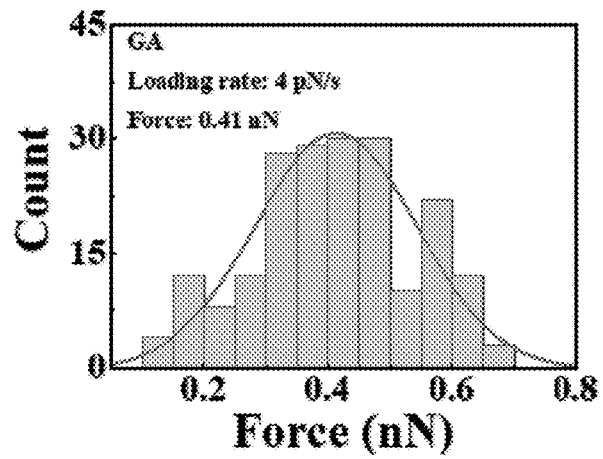
Figure 11C:
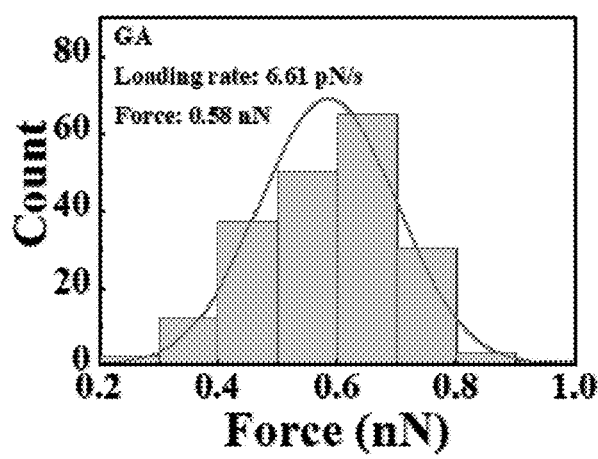
Figure 11D:
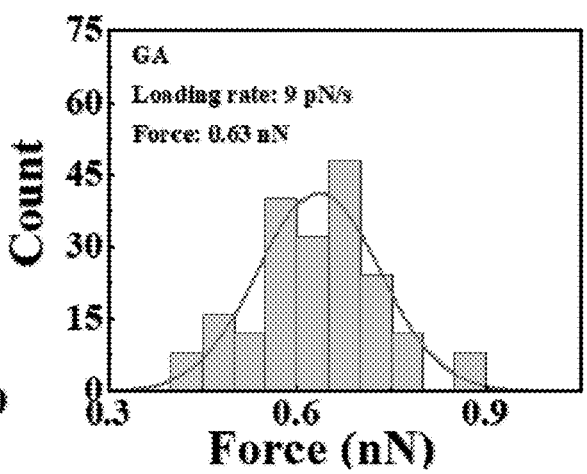
Figure 12A:
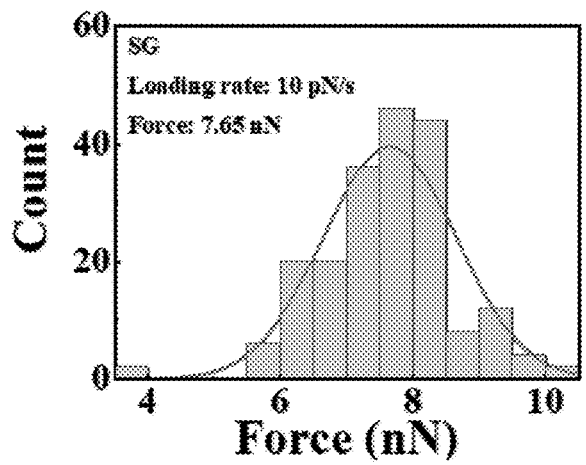
Figure 12B:
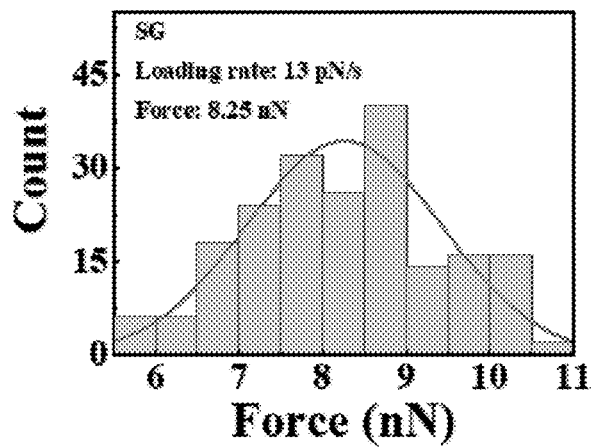
Figure 12C:
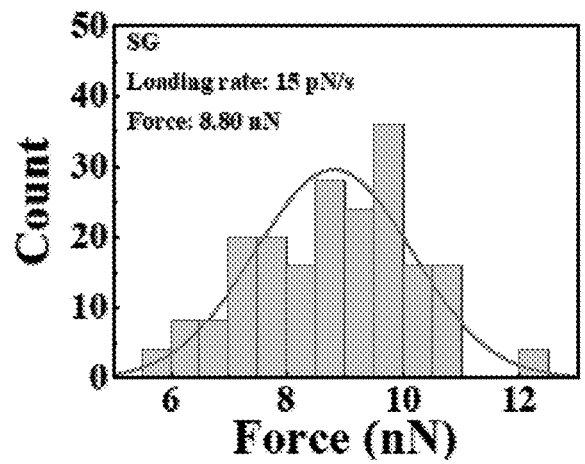
Figure 12D:
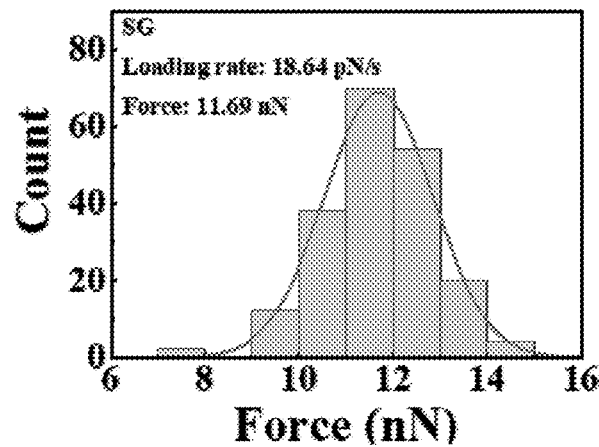
Figure 13A:
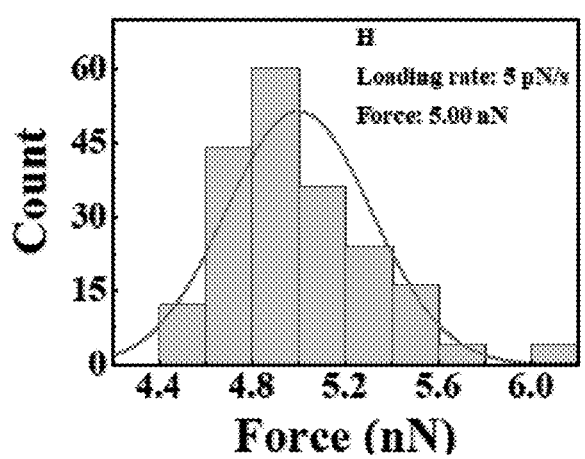
FIGS. 13A-13F are the force statistical histogram and dissociation rate fitting diagram of H and cellulase at different loading force speeds.
Figure 13B:
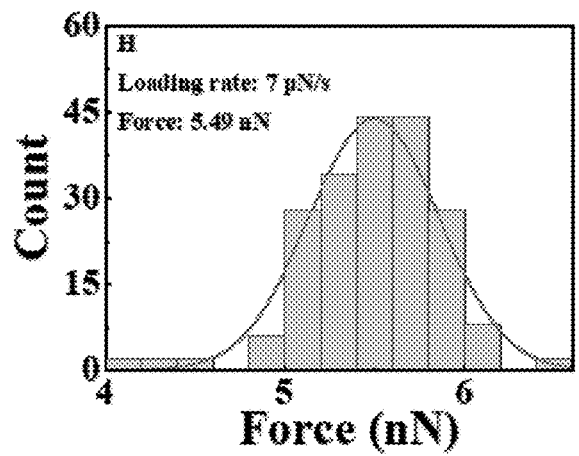
Figure 13C:
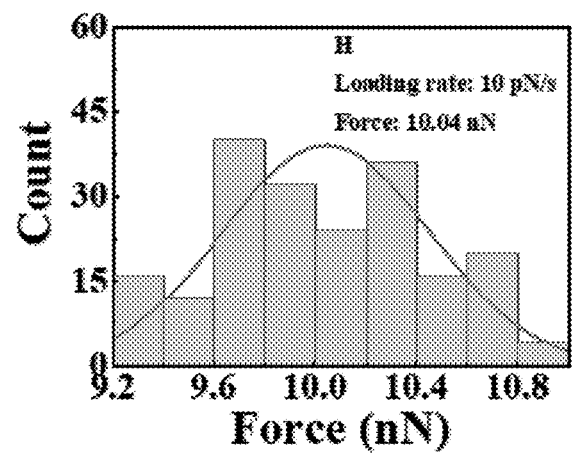
Figure 13D:
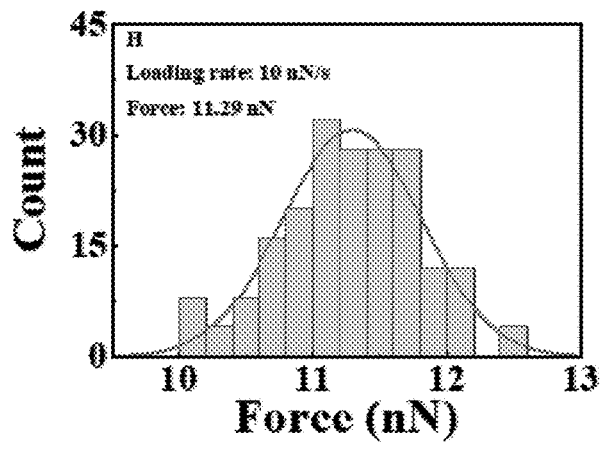
Figure 13E:
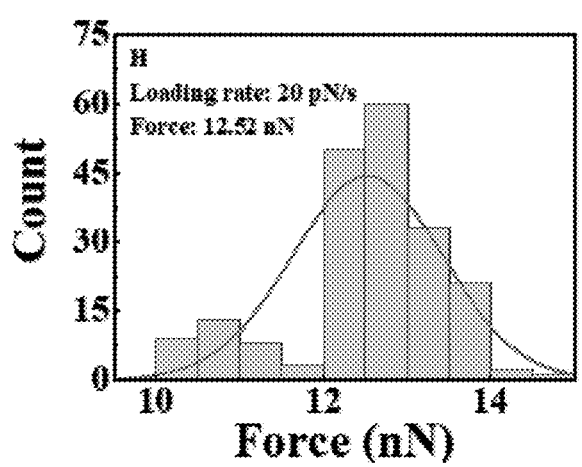
Figure 13F:
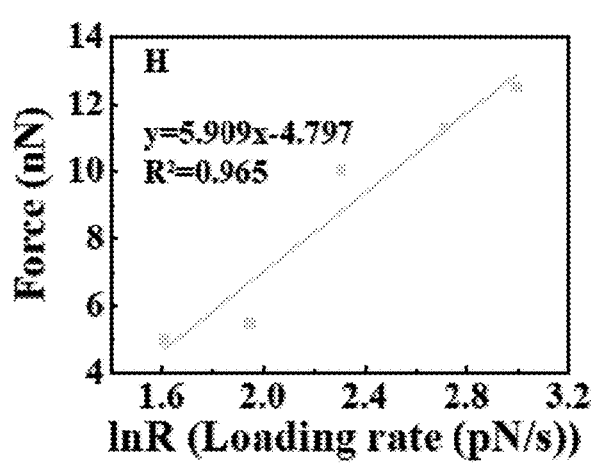
Figure 14A:
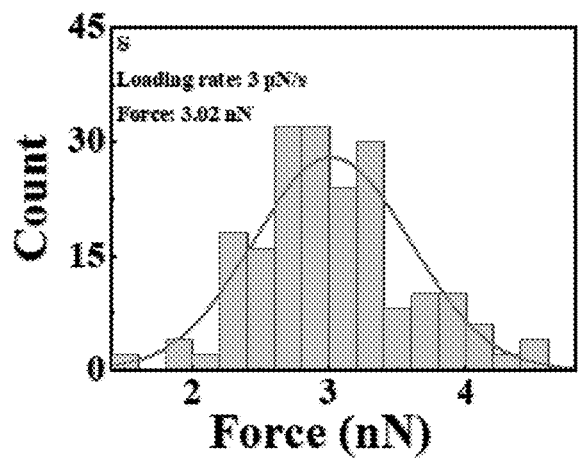
FIGS. 14A-14F are the force statistical histogram and dissociation rate fitting diagram of S and cellulase at different loading force speeds.
Figure 14B:
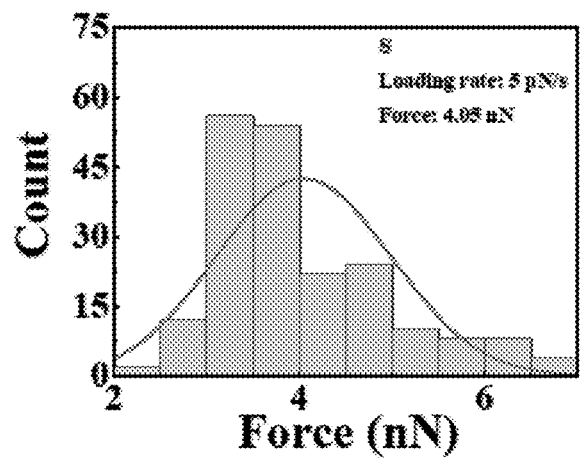
Figure 14C:
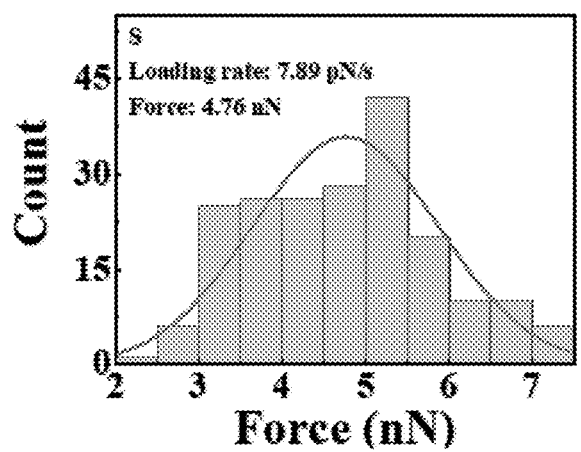
Figure 14D:
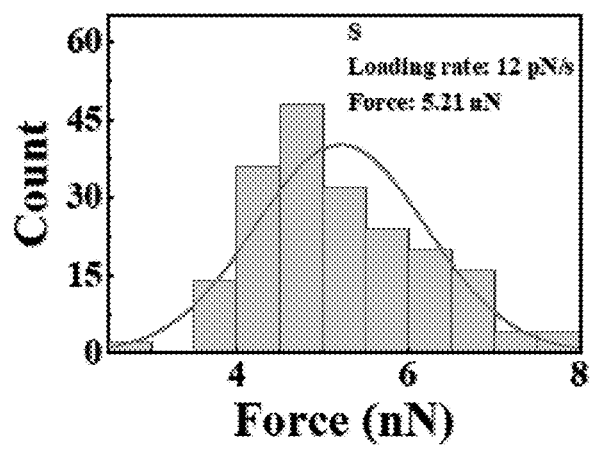
Figure 14E:
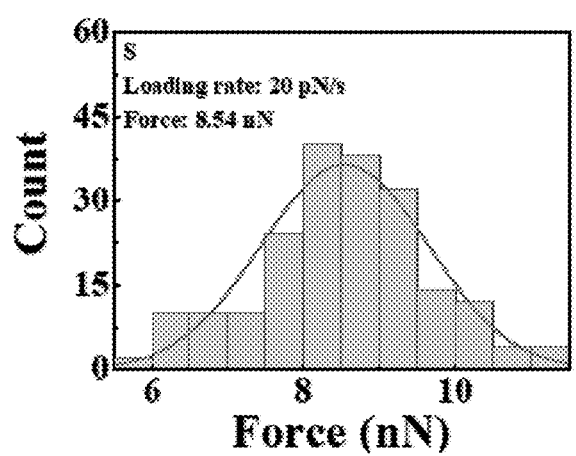
Figure 14F:
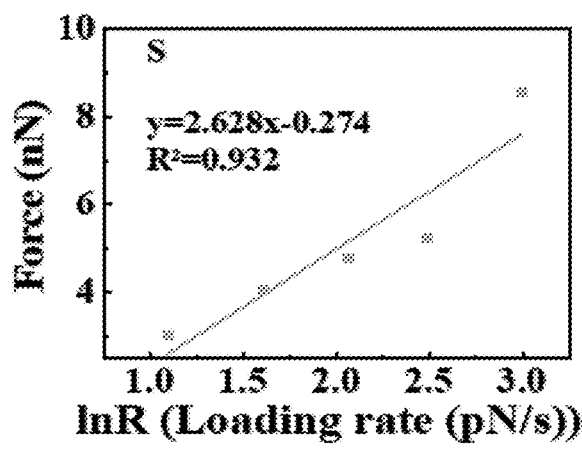
Figure 15A:
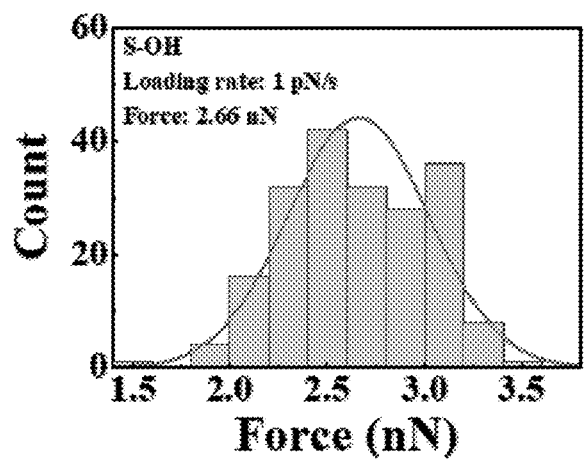
FIGS. 15A-15F are the force statistical histogram and dissociation rate fitting diagram of S—OH and cellulase at different loading force speeds.
Figure 15B:
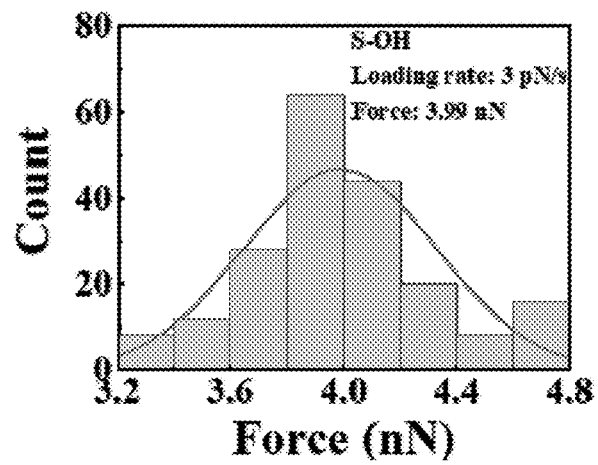
Figure 15C:
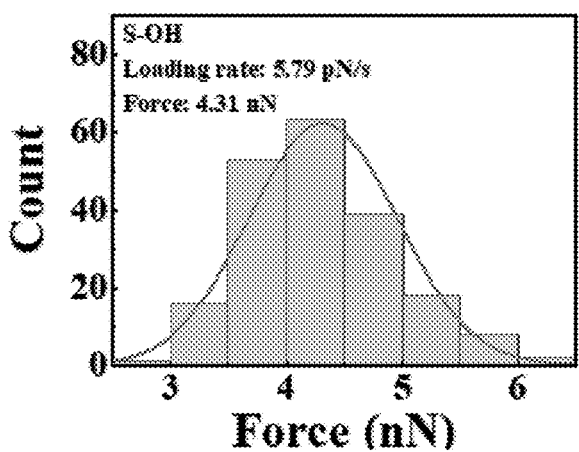
Figure 15D:
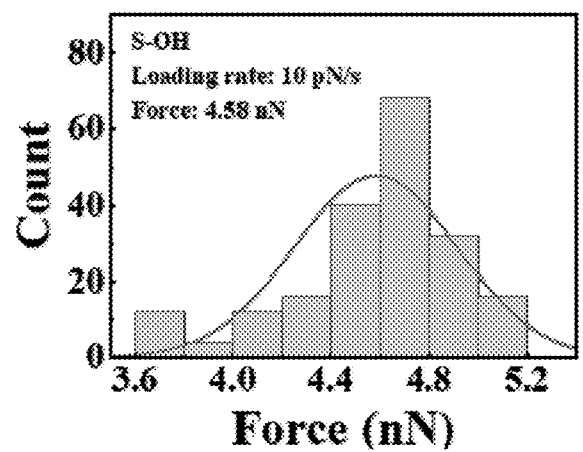
Figure 15E:
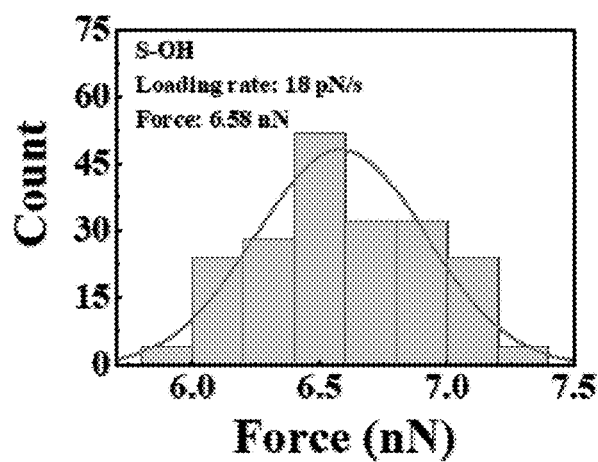
Figure 15F:
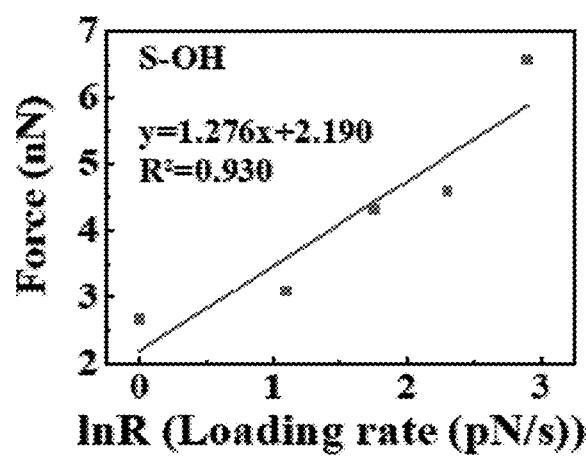

Example 2: Analysis of the Interaction Force Between Lignin Model Substance and Cellulase in Liquid Phase Environment 1. Preparation of lignin film: The names of 7 different lignin model substances were labelled as GG, G, GA, SG, H, S, and S—OH according to the corresponding structural formulas (see FIG. 6). 0.5% (w/v, DMSO) solutions of different lignin model substances were prepared, then 100 μL of the solution was dropwise added onto the silicon wafer with a flat mouth syringe, after the solution diffused to the entire surface of the silicon wafer, it was left for 1 min, and a spin coater (KW-4A, Shanghai Daojing Instrument Factory, China) was used to spin coat at a speed of 5000 r/min for 1 min, and repeat 3 times. The prepared lignin film was vacuum dried at 40° C. for 4 h, and then soaked in deionized water for 1 day. The deionized water was replaced every 2 h to ensure that DMSO was completely removed to avoid affecting the activity of cellulase. The soaked film was vacuum dried at 40° C. for 12 h.
2. AFM probe modification: The AFM probe with a gold film on the surface was immersed in a 0.2 mg/mL HS-PEG-COOH DMSO solution and incubated at room temperature for 3 h in the dark. After washing the PEG-modified probe with DMSO three times, it was placed in warm water below 50° C. and allowed to stand for 30 min to remove the PEG molecules physically adsorbed on the probe surface. Then the AFM probe was immersed in a 10 mM NHS/EDC mixed PBS buffer and incubated at room temperature for 30 min. The carboxyl-activated AFM probe was immersed in a PBS solution of cellulase (0.2 μM, pH=7.4) and incubated overnight at 4° C. in the dark. After the modification, the AFM probe was washed three times with PBS solution and placed in PBS buffer solution for storage for later use.
3. Test of the interaction force between lignin model substance and cellulase in liquid phase environment: The morphologies of the surface lignin and residual lignin of the hydrothermally pretreated poplar wood fixed on the silicon wafer surface at different temperatures were obtained by using the AC Air Topography and AC Water Topography modes of the AFM instrument (MFP-3D origin, Asylum research, Oxford Instruments, UK) (FIG. 7).

Subsequently, in a liquid phase environment, the AFM contact mode was used to measure the interaction force between the AFM probe modified by cellulase and different lignin model substances, the force-displacement curves and the action force-displacement curves between cellulase and different lignins (FIGS. 8A-8G). After counting 200 representative force-displacement curves at each loading rate, the dissociation force between the lignin model substance and the cellulase was calculated using the following Bell-Evans equation:

$$F = \frac{k_B T}{x_\beta} \times \ln \frac{R x_\beta}{k_B T k_{off}} \quad (1)$$

Where F represents the dissociation force, $X_\beta$ is the distance from the lowest energy point of the binding state to the molecular activation state on the dissociation path, R is the dissociation force loading rate, $R = k_{eff} \times v$, where $k_{eff}$ is the effective elastic coefficient of the AFM probe cantilever, and v is the retraction rate of the probe, $k_{off}$ is the dissociation rate constant when the lignin-cellulase interaction force is zero, T is the thermodynamic temperature, and $k_B$ is the Boltzmann constant.

As shown in FIGS. 8A-8G, the interaction forces between the seven different lignin model substances GG, G, GA, SG, H, S, and S—OH and cellulase are 2.59 nN, 0.97 nN, 0.58 nN, 11.69 nN, 12.52 nN, 4.76 nN, and 4.31 nN, respectively. The results show that the maximum interaction force between the H-type lignin model substance and cellulase is 12.52 nN. The second is the interaction force between the SG-type lignin model substance and cellulase (11.69 nN). In addition, the interaction forces of the three representative lignin structural units and cellulase are H>S>G. Overall, the interaction force of dimers on cellulase is stronger than the interaction force of monomeric model substances on cellulase.

In addition, the binding ability of lignin model substance with cellulase can also be evaluated by the dissociation rate constant of the interaction reaction. At the single molecule level, AFM can be used to detect the dissociation rate of the interaction between the lignin model substance molecules modified on the substrate and the cellulase protein modified on the tip of the AFM probe. The force histograms and dissociation rate fitting diagrams of different lignin model substances and cellulase at different force loading rates are shown in FIGS. 9A-15F.

As shown in FIGS. 9A-9F, the most likely dissociation forces of GG and cellulase at five different loading force rates (5 pN/s, 10 pN/s, 15 pN/s, 20 pN/s, 24.24 pN/s) were 1.65 nN, 1.92 nN, 2.27 nN, 2.46 nN, and 2.59 nN, respectively. As shown in FIGS. 10A-10F, the most likely dissociation forces between G and cellulase at five different loading rates (1 pN/s, 3 pN/s, 5.74 pN/s, 7 pN/s, 12 pN/s) were 0.39 nN, 0.87 nN, 0.97 nN, 1.06 nN, and 1.25 nN, respectively. As shown in FIGS. 11A-11F, the most likely dissociation forces between GA and cellulase at five different loading rates (3 pN/s, 4 pN/s, 6.61 pN/s, 9 pN/s, and 10 pN/s) were 0.39 nN, 0.41 nN, 0.58 nN, 0.63 nN, and 0.88 nN, respectively. As shown in FIGS. 12A-12F, the most likely dissociation forces between SG and cellulase at five different loading rates (10 pN/s, 13 pN/s, 15 pN/s, 18.64 pN/s, 23 pN/s) were 7.65 nN, 8.25 nN, 8.80 nN, 11.69 nN, and 13.40 nN, respectively. As shown in FIGS. 13A-13F, the most likely dissociation forces between H and cellulase at five different loading rates (5 pN/s, 7 pN/s, 10 pN/s, 15 pN/s, and 20 pN/s) were 5.00 nN, 5.49 nN, 10.04 nN, 11.29 nN, and 12.52 nN, respectively. As shown in FIGS. 14A-14F, the most likely dissociation forces between S and cellulase at five different loading rates (3 pN/s, 5 pN/s, 7.89 pN/s, 12 pN/s, 20 pN/s) were 3.02 nN, 4.05 nN, 4.76 nN, 5.21 nN, and 8.54 nN, respectively. As shown in FIGS. 15A-15F, the most likely dissociation forces between S—OH and cellulase at five different loading rates (1 pN/s, 3 pN/s, 5.79 pN/s, 10 pN/s, and 18 pN/s) were 2.66 nN, 3.99 nN, 4.31 nN, 4.58 nN, and 6.58 nN, respectively.

In order to calculate the dissociation rate constant ($k_{off}$) of the interaction between lignin modified on the substrate surface and cellulase, the Bell-Evans model of formula 1 was used to perform linear fitting with lnR as the horizontal coordinate and F as the vertical coordinate. The results are shown in Table 2. As shown in Table 2, the dissociation rates of GG, G, GA, SG, H, S, and S—OH are 1.77 s$^{-1}$, 3.23 s$^{-1}$, 3.11 s$^{-1}$, 0.15 s$^{-1}$, 0.18 s$^{-1}$, 0.41 s$^{-1}$, and 0.85 s$^{-1}$, respectively. The low dissociation rate constant indicates that the lignin modified on the substrate surface has a higher affinity with the cellulase, that is, the less likely it is to dissociate after the two are combined. The above data shows that SG is the least likely to dissociate after combining with cellulase. In addition, the dissociation rate of the lignin model substance containing S-type units is lower than that of the lignin model substance containing G-type units.

In summary, the above results prove that the AFM method can be used to evaluate the interaction force and dissociation rate between different lignin model substances and cellulase in a liquid environment, which is conducive to further analyzing the interaction mechanism between lignin and cellulase, laying a solid theoretical foundation for the next step of scientific research and has good practicality.

TABLE 2

Dissociation rates of different lignin model substances and cellulase

| System | $F_{eq}$ (nN) | $k_{off}$ (s$^{-1}$) |
|---|---|---|
| GG-cellulase | 2.59 | 1.77 |
| G-cellulase | 0.97 | 3.23 |
| GA-cellulase | 0.58 | 3.11 |
| SG-cellulase | 11.69 | 0.15 |
| H-cellulase | 12.52 | 0.18 |
| S-cellulase | 4.76 | 0.41 |
| S-OH-cellulase | 4.31 | 0.85 |

What is claimed is:

1. A method for characterizing an interaction force between a lignin model substance and cellulase, comprising the following steps:
    (1) a preparation of a lignin model substance film: preparing a 0.5% lignin model substance solution, then dropwise adding 100 μL of the 0.5% lignin model substance solution on a silicon wafer using a flat mouth syringe, after the 0.5% lignin model substance solution diffuses to an entire silicon wafer surface, allowing the silicon wafer to stand for 1 min, and using a spin coater to spin-coat at a speed of 5000 r/min for 1 min, with 3 repeats; vacuum-drying a prepared lignin film at 40° C. for 4 h, and then soaking a dried lignin film in deionized water for 1 day; replacing the deionized water every 2 h to remove dimethylsulfoxide (DMSO); vacuum-drying a soaked film at 40° C. for 12 h;

wherein a lignin model substance is one or more of the following substances:

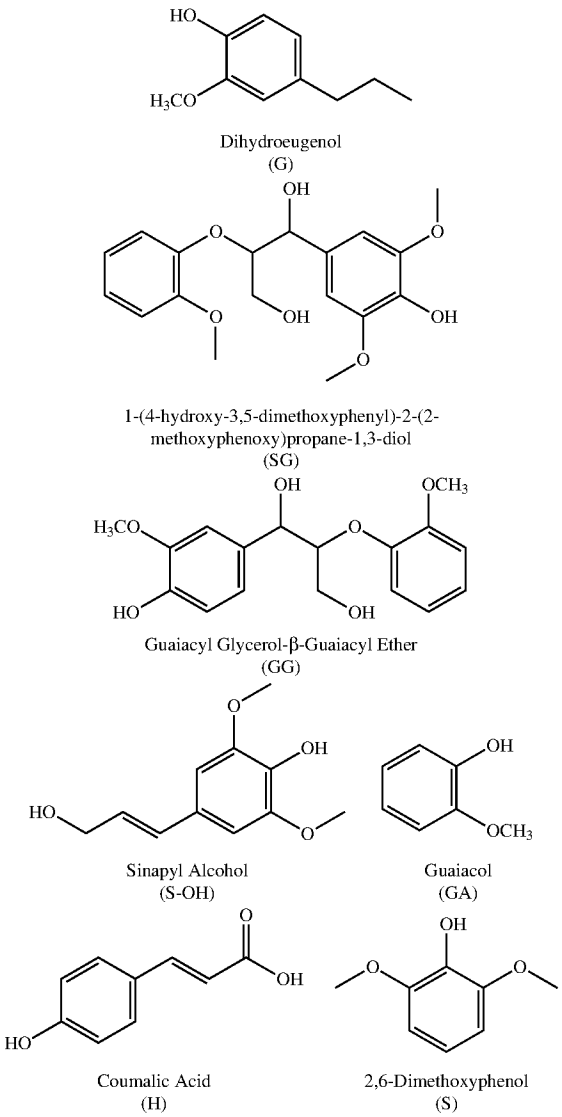

Dihydroeugenol (G)

1-(4-hydroxy-3,5-dimethoxyphenyl)-2-(2-methoxyphenoxy)propane-1,3-diol (SG)

Guaiacyl Glycerol-β-Guaiacyl Ether (GG)

Sinapyl Alcohol (S-OH)

Guaiacol (GA)

Coumalic Acid (H)

2,6-Dimethoxyphenol (S)

(2) an atomic force microscopy (AFM) probe modification: modifying an AFM probe coated with a gold film on a surface with HS-PEG-COOH and then activating a carboxyl group, immersing the AFM probe after a carboxyl group activation in a phosphate buffer saline (PBS) solution of the cellulase for an incubation, and after the AFM probe modification is completed, placing a washed AFM probe in a PBS buffer solution for a storage and a later use;

(3) using an AFM instrument to test a lignin model substance-cellulase interaction force in a liquid phase environment: detecting a dissociation rate of the interaction between the lignin model substance molecules modified on the film and the cellulase protein modified on the tip of the AFM probe, evaluating a binding ability of the lignin model substance and the cellulase by a dissociation rate constant of an interaction reaction, and after counting a number of representative force-displacement curves at each loading rate, calculating a dissociation force between the lignin model substance and the cellulase using the following Bell-Evans equation:

$$F = \frac{k_B T}{x_\beta} \times \ln\frac{Rx_\beta}{k_B T k_{off}}$$

wherein F represents the dissociation force, $X_\beta$ is a distance from a lowest energy point of a binding state to a molecular activation state on a dissociation path, R is a dissociation force loading rate, $R = k_{eff} \times v$, where $k_{eff}$ is an effective elastic coefficient of an AFM probe cantilever, and v is a retraction rate of the AFM probe, $k_{off}$ is a dissociation rate constant when the lignin model substance-cellulase interaction force is zero, T is a thermodynamic temperature, and $k_B$ is a Boltzmann constant.

2. The method for characterizing the interaction force between the lignin model substance and the cellulase according to claim 1, wherein a specific method of modifying the AFM probe is as follows:

the AFM probe with the gold film on the surface is immersed in a DMSO solution of 0.2 mg/ml HS-PEG-COOH and incubated at a room temperature in a dark for 3 h; a polyethylene glycol (PEG)-modified probe is washed three times with the DMSO, placed in a warm water less than 50° C., and left for 30 min to remove PEG molecules physically adsorbed on the surface of the AFM probe; then the AFM probe is immersed in a 10 mM N-Hydroxysuccinimide (NHS)/1-(3-Dimethylaminopropyl)-3-ethylcarbodiimide (EDC) mixed PBS buffer and incubated at the room temperature for 30 min; a carboxyl-activated AFM probe is immersed in the PBS solution of the cellulase and incubated overnight in the dark at 4° C.; after the AFM probe modification is completed, the AFM probe is washed three times with a PBS solution and placed in the PBS buffer solution for the storage and the later use.

3. The method for characterizing the interaction force between the lignin model substance and the cellulase according to claim 2, wherein a molar mass of the PBS solution of the cellulase is 0.2 μM and pH=7.4.

* * * * *